US006212420B1

(12) United States Patent
Wang et al.

(10) Patent No.: US 6,212,420 B1
(45) Date of Patent: Apr. 3, 2001

(54) CURVED CROSS-SECTION BASED SYSTEM AND METHOD FOR GASTROINTESTINAL TRACT UNRAVELING

(75) Inventors: Ge Wang, Iowa City, IA (US); Elizabeth G. McFarland, Chesterfield, MO (US); Bruce P. Brown, Iowa City, IA (US); Zhan Zhang, Iowa City, IA (US); Michael W. Vannier, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/267,183

(22) Filed: Mar. 12, 1999

Related U.S. Application Data

(60) Provisional application No. 60/077,851, filed on Mar. 13, 1998.

(51) Int. Cl.[7] .................................................. A61B 5/05
(52) U.S. Cl. ............................................. 600/407; 382/128
(58) Field of Search .................................. 600/407, 425; 382/128, 131

(56) References Cited

U.S. PATENT DOCUMENTS

| 4,939,646 | * | 7/1990 | Essinger et al. ..................... 382/128 |
| 5,458,111 | | 10/1995 | Coin . |
| 5,699,799 | | 12/1997 | Xu et al. . |
| 5,891,030 | * | 4/1999 | Johnson et al. ..................... 600/407 |

OTHER PUBLICATIONS

Hara, et al., Detection of Colorectal Polyps by Computed Tomographic Colography: Feasibility of a Novel Technique, *American Gastroenterological Association*, 1996.

McFarland, et al., "Spiral Computed Tomographic Colonography: Determination of the Central Axis and Digital Unraveling of the Colon", *Acad Radiol.*, 1997; 4:367–373.

Wang, et al., "GI Tract Unraveling with Curved Cross Sections", *IEEE Transactions on Medical Imaging*, vol. 17, No. 2, Apr. 1998.

Wang, G, Vannier, MW, "GI Tract Unraveling by Spiral CT," Proc. SPIE vol. 2434, p. 307–315, Medical Imaging 1995: Image Processing, Murray H. Loew, Ed., May, 1995.

* cited by examiner

*Primary Examiner*—John A. Jeffery
(74) *Attorney, Agent, or Firm*—Needle & Rosenberg, P.C.

(57) ABSTRACT

The present invention is directed towards an improved system and method for visualizing and quantifying data associated with biological curvilinear/tubular structures such as the gastrointestinal tract.

In the present invention, an electrical field based approach provides a system and method to unravel convoluted biological curvilinear/tubular structures such as the colon. The approach digitally straightens or flatten such structures with curved cross-sections. Electrical charges are simulated along the structure's central path. Each curved cross-section of the colon is defined by electrical force lines due to charges distributed along the colon path, and constructed by directly tracing the force lines. In a further embodiment, the efficiency of the unraveling is improved by directly tracing only representative force lines that originate equiangularly from the current colon path position. The other force lines are interpolated from the traced force lines.

15 Claims, 20 Drawing Sheets

STRAIGHTENING FLOWCHART

STRAIGHTENING FLOWCHART

DISTORTION RESULTING FROM ELECTRICAL FIELD MODEL

REPRESENTATIVE IMAGES FOR HARD STRAIGHTENING
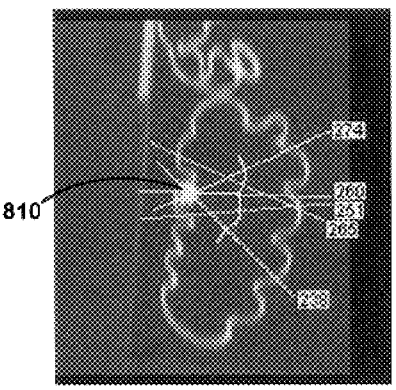
FIG.7A
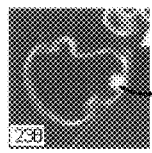 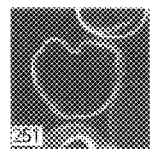 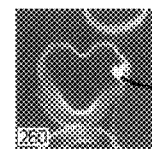 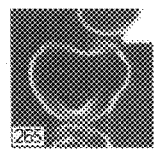 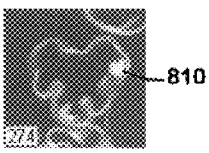
FIG.7B   FIG.7C   FIG.7D   FIG.7E   FIG.7F REPRESENTATIVE IMAGES FOR SOFT STRAIGHTENING:
PARTIAL ELECTRICAL FIELD LENGTH L=9
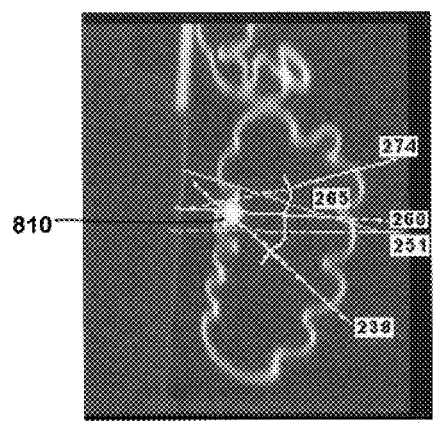
FIG.8A
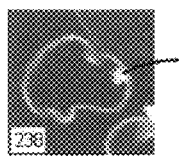 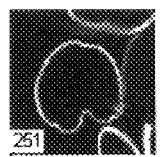 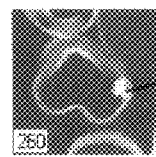 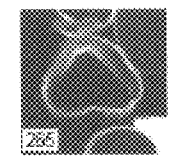 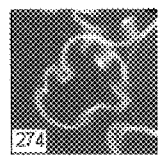
FIG.8B  FIG.8C  FIG.8D  FIG.8E  FIG.8F REPRESENTATIVE IMAGES FOR SOFT STRAIGHTENING:
PARTIAL ELECTRICAL FIELD LENGTH L=15
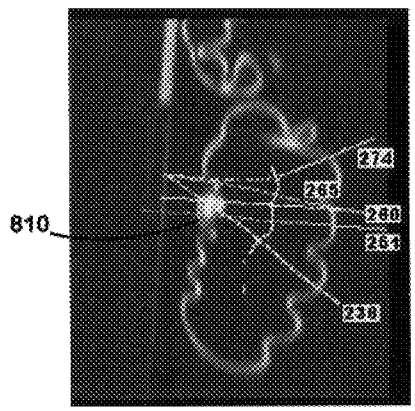
FIG.9A
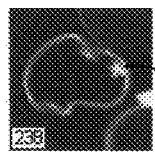 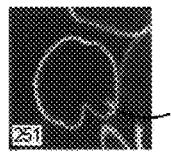 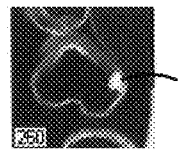 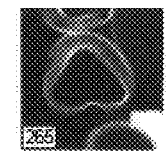 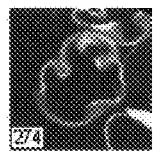
FIG.9B   FIG.9C   FIG.9D   FIG.9E   FIG.9F

REPRESENTATIVE IMAGES OF PATIENT DATA
USING HARD STRAIGHTENING (L=0)
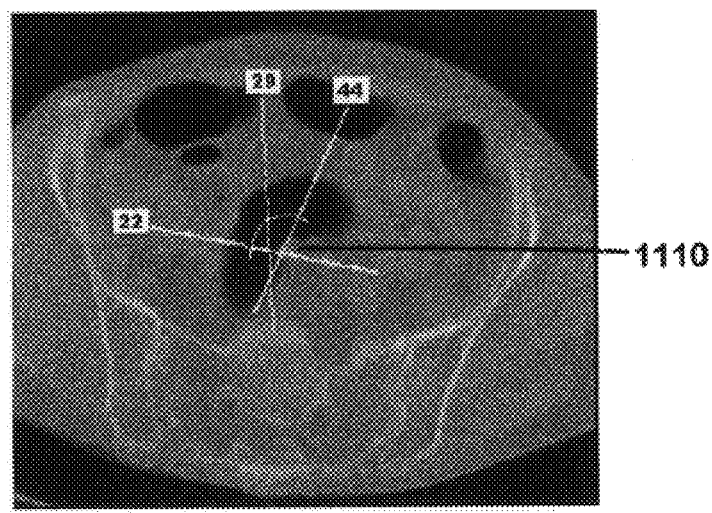
FIG.10A
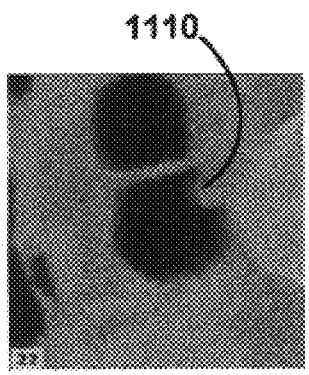 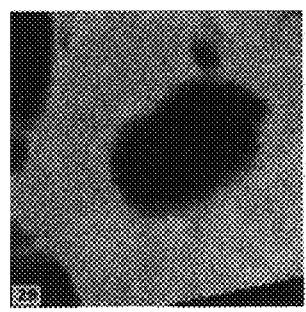 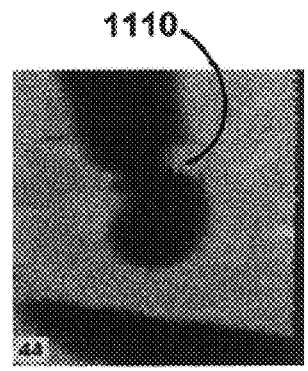
FIG.10B     FIG.10C     FIG.10D

REPRESENTATIVE IMAGES OF PATIENT DATA
USING SOFT STRAIGHTENING (L=21)

VISUALIZING SOFT STRAIGHTENED COLON PHANTOM

VISUALIZING SOFT STRAIGHTENED PATIENT DATA

ORTHOGONAL PLANE WITH RESPECT TO
A CENTRAL PATH POINT

TRACING RESULT FOR AN ELECTRICAL FORCE LINE

FLOWCHART OF ACCELERATED SOFT-STRAIGHTENING

STRAIGHTENED COLON PHANTOM USING
FORCE LINE INTERPOLATION APPROACH

STRAIGHTENED PATIENT COLON USING
FORCE LINE INTERPOLATION APPROACH

DEFINITION OF CONFLICT BETWEEN ADJACENT CROSS-SECTIONS

IDENTIFYING DIFFERING LESIONS IN ELECTRICAL
FEILD-BASED SOFT-STRAIGHTENED COLON

CURVED CROSS-SECTION BASED SYSTEM AND METHOD FOR GASTROINTESTINAL TRACT UNRAVELING

CROSS-REFERENCE TO RELATED PATENT APPLICATION

This application claims the benefit, pursuant to 35 U.S.C. § 120, of applicants' provisional U.S. patent application Ser. No. 60/077,851, filed Mar. 13, 1998, entitled "GI Tract Unraveling with Curved Cross-Sections".

ACKNOWLEDGMENT

This invention was made with government support under NIDDK R29 DK50184 awarded by the National Institutes of Health. The government has certain rights in the invention.

BACKGROUND OF THE INVENTION

1. Field of Invention

The present invention generally relates to a system and method for unraveling biological curvilinear/tubular structures utilizing curved cross-sections.

2. Description of Prior Art

Disorders of the GI tract are common, including neoplasms, inflammatory diseases, post-operative complications, malabsorption, infectious and ischemic diseases. Colorectal carcinoma is the third cause of cancer death in the United States, common in other Western countries and increasing rapidly in the East where Western life-styles are being adopted. It was estimated that 109,000 new diagnoses of colon cancer and 43,000 of rectal cancer were made in 1993, divided almost equally between males and females. In the same year approximately 50,000 patients died of colon cancer and 7,000 of rectal cancer. Inflammatory bowel diseases affect nearly two million Americans, and almost 10,000 new cases each of ulcerative colitis and Crohn's disease are diagnosed annually in the United States alone. Although inflammatory bowel diseases are more frequent in developed areas of the world, there are no racial boundaries limiting their incidence.

Fiberoptic colonoscopy currently represents the most sensitive imaging examination of the colonic mucosa to detect lesions. However, colonoscopy is invasive, quite expensive, carries a small risk of perforation, involves sedation, and in some cases fails to visualize the entire colon. With the advent of spiral computed tomography CT, CT colography (CTC) has attracted increasing attention as an alternative to the traditional colonoscopy for 3D visualization of the colon.

GI tract diagnosis has relied on X-ray imaging since early this century, and has been a major impetus for the development of better technology and methods. GI imaging has undergone several revolutionary changes in the past two decades, especially X-ray CT, magnetic resonance imaging (MRI), endoscopy, and endosonography.

X-ray CT is an established cost-effective imaging modality that produces sectional and volumetric maps of linear X-ray attenuation coefficient. Spiral (or helical) CT is a major advance in X-ray CT in which source rotation and patient translation are simultaneously and continuously conducted, resulting in a helical scanning locus with respect to a patient.

The advantages of spiral CT are volumetric scanning within a single breath-hold and retrospective position selection for transaxial slice reconstruction. Fast scanning eliminates slice-to-slice misregistration, since projection data are rapidly acquired at a consistent inspiration level. Typically, a 30 cm long volume can be covered in 15 to 30 seconds. Retrospective reconstruction allows overlapped transaxial slices and thus provides improved longitudinal resolution as compared to conventional incremental CT (step and shoot). In conventional CT, there are fewer reconstructed slices available, and features with sizes comparable to the slice thickness may be missed or distorted. Spiral CT decreases the radiation hazard since the maximum amount of radiation dose delivered to individual voxels is minimized. Recognized for these advantages, spiral CT has gained general acceptance as the standard medical CT mode. Currently spiral CT abdominal scans are routinely done nationwide.

Spiral CT allows coverage of the entire colon within a breath-hold acquisition. From this volumetric data set, 3D volume rendering algorithms can be employed to perform the "virtual" endoscopic visualization of the mucosal surface of the colon for detection of colorectal polyps, precursors of cancer. These techniques require navigation through the tortuous anatomy of the colon, which can be time consuming in practice.

Conceptually, the current CTC may be viewed as a two-step process: navigation and visualization. In other words, a curvilinear colon path must be first determined either interactively or automatically, then the colonic mucosa is visualized after either surface or volume rendering. This method produces excellent internal views in a cine loop, but it can be difficult to use and time consuming, since the colon is highly convoluted.

In G. Wang, M. W. Vannier, "Unraveling the GI tract by spiral CT," SPIE 2434, pp. 307–315, 1995, a shift from slice-based GI tract examination to unraveled GI tract examination was proposed. At that time, GI tract examination with CT and MRI was commonly interpreted by slice-based visual inspection despite the volumetric nature of the anatomical components, tumors/lesions and imaging modalities.

The slice-based interpretation primarily has two limitations. First, global comprehension of GI components and tumors/lesions are often difficult; and, second, quantification is impossible due to subjective interpretive error sources. The proposed spiral CT abdominal image visualization and analysis system utilizing an unraveling system based upon use of planar cross-sections orthogonal to the central path of the curvilinear/tubular structure was better suited to handle the highly convoluted GI tract. The system straightened and flattened convoluted portions of the GI tract via computer post-processing of the CT data. Using such a system has potential to improve diagnostic performance by providing intuitive and quantitative pathologic information.

An unraveling approach allows the manipulation the GI tract virtually and the derivation of pathological information quantitatively and automatically. An advantage of this approach is the direct visualization of the colon surface, without the need for navigation. Also, the image unraveling utilities can be combined with virtual reality techniques and conventional orthogonal sections for greater visualization freedom.

However, the progress on unraveling of the GI tract has been limited by substantial artifacts from unraveling with planar cross-sections orthogonal to the central path. Specifically, a fundamental difficulty with unraveling convoluted structures such as the colon is that resampling along intersecting image planes can result in discontinuities, misregistration, multiple counting or total missing of polyps.

When planar cross-sections with respect to the colon path are stacked, the tortuous colon is straightened, which is referred to as "hard" straightening. Hard straightening is satisfactory in regions where the colon is linear, but stacking transverse sections of a curved lumen can produce double sampling of some regions and inadequate sampling of other regions, especially at sharp turns or kinks in the lumen. FIG. 1 demonstrates these problems. In FIG. 1A, a single polyp 110 along the inner curve can appear in several sections 120, be missed in subsequent sections 130 and be sampled again in later sections 140. In this way as seen in FIG. 1B, one polyp 150 appears as two polyps, "double counting" occurs. For the same reasons, a polyp 160 along the outer portion of a curve may not be sampled and will be missed entirely.

"Soft" straightening/unraveling techniques were developed to overcome the limitations of hard straightening. In soft straightening, cross-sections with respect to the colon path are curved appropriately so that these slices do not conflict with each other.

SUMMARY OF THE INVENTION

The present invention is directed towards an improved system and method for visualizing and quantifying data associated with biological curvilinear/tubular structures such as the gastrointestinal tract.

In the present invention, an electrical field based approach serves as an example for use of a physical analogy to consistently unravel a curvilinear structure, and provides a system and method to unravel convoluted biological curvilinear/tubular structures such as the colon. The key idea here is use of curved cross-section, while the physical model is not unique. The approach digitally straightens such structures with curved cross-sections and flattens them over a plane. Electrical charges are simulated along the structure's central path. Each curved cross-section of the colon is defined by electrical force lines due to charges distributed along the colon path, and constructed by directly tracing the force lines.

In a further embodiment, the efficiency of the unraveling is improved by directly tracing only representative force lines that originate equiangularly from the current colon path position. The other force lines are interpolated from the traced force lines.

BRIEF DESCRIPTION OF THE DRAWINGS

FIG. 7A displays the orientation of 5 slices as identified by the slice numbers 238, 251, 260, 265, 274, respectively, along the 285 point central path, and the central path as seen in a sagittal plane of the original volume with electric field length parameter L=0.

FIGS. 7B–7F display the views at the 5 selected slices as shown in FIG. 7A with electric field length parameter L=0, respectively.

FIG. 8 depicts representative images for soft straightening with partial electrical field length L=9 of the phantom data set.

FIG. 8A displays the orientation of 5 slices as identified by the slice numbers 238, 251, 260, 265, 274, respectively, along the 285 point central path, and the central path as seen in a sagittal plane of the original volume with electric field length parameter L=9.

FIGS. 8B–8F display the views at the 5 selected slices as shown in FIG. 8A with electric filed length parameter L=9.

FIG. 9A displays the orientation of 5 slices as identified by the slice numbers 238, 251, 260, 265, 274, respectively, along the 285 point central path, and the central path as seen in a sagittal plane of the original volume with electric field length parameter L=15.

FIGS. 9B–9F display the views at the 5 selected slices as shown in FIG. 9A with electric field length parameter L=15, respectively.

FIG. 10A illustrates an image of an actual patient data set showing a polyp 1110 near a bend being counted twice using hard straightening (electric field length parameter L=0).

FIGS. 10B–10D display the views at 3 selected slices through central path points 22, 29 and 44 as shown in FIG. 10A with electric field length parameter L=0, respectively.

DETAILED DESCRIPTION OF THE INVENTION

The GI tract unraveling task can be decomposed into two subtasks: central path determination and cross-section formation. The central path determination subtask can be performed manually, automatically or semi-automatically. In a preferred embodiment, the central path determination is accomplished semi-automatically using an IDL program; this central path determination method fits a GI tract central path through a sequence of user selected intraluminal points using cubic spline interpolation. GI tract tracking follows the fitted central path. Then, cross-sections should be formed to straighten the GI tract and open it into a flat image volume for further analyses.

Figure 1A:
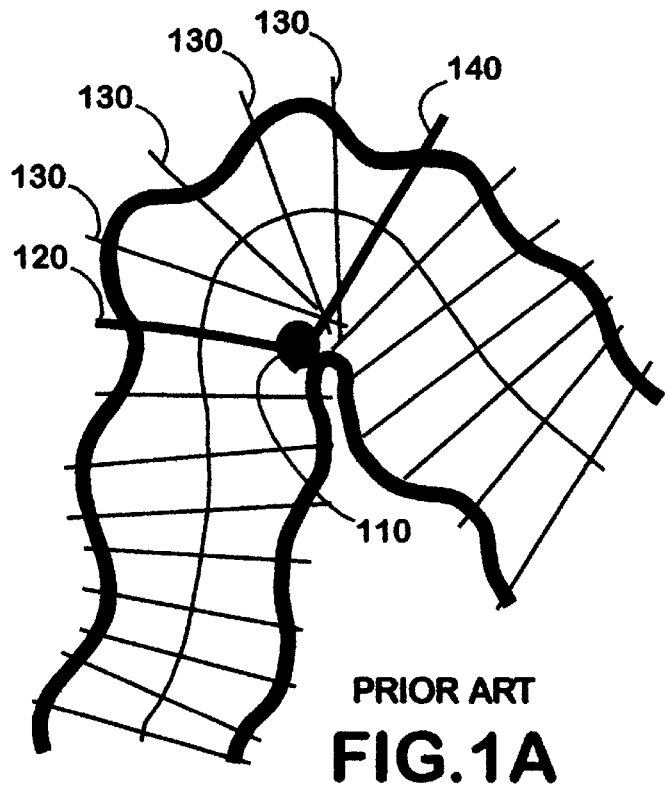
FIG. 1A illustrates potential problems with planar cross sections of a sharp turn in the GI tract.
Figure 1B:
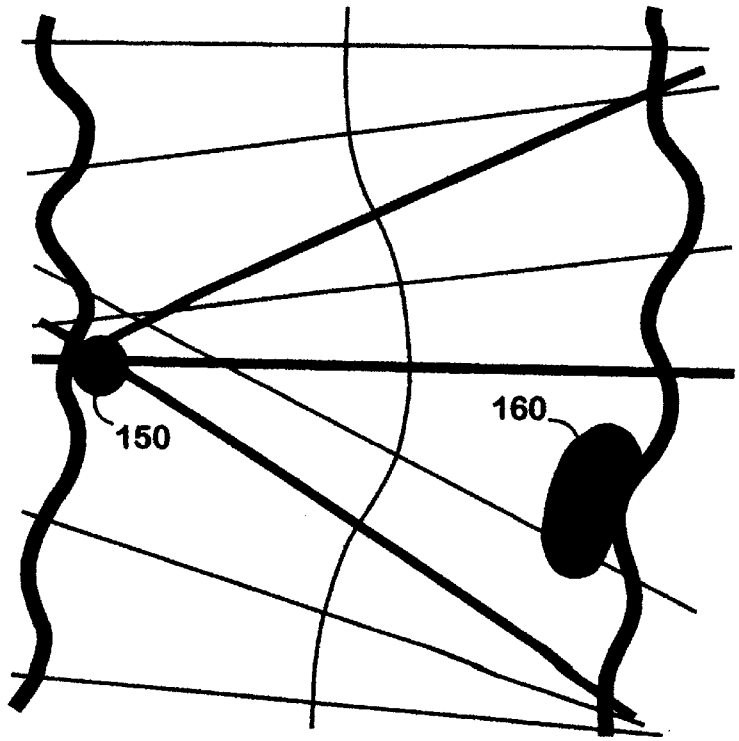
FIG. 1B illustrates potential problems with planar cross section of a kink in the GI tract.
Figure 2A:
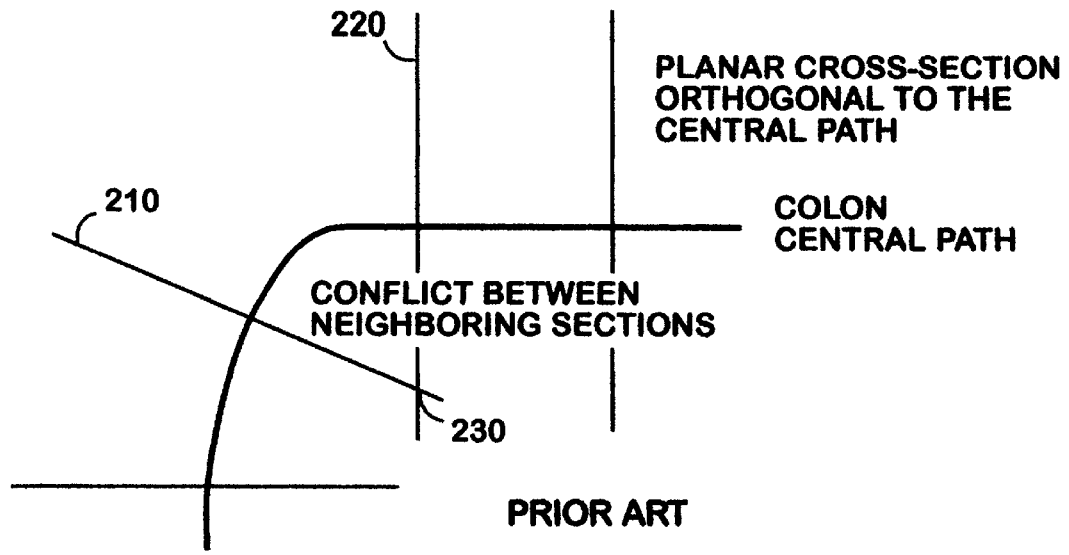
FIG. 2A displays the potential conflict between neighboring planar cross sections.

The simplest colon cross-sections are oblique sections that are planar and orthogonal to the colon central path. However, if the central path bends substantially, nearby cross-sections may well conflict as seen in FIG. 2A. A satisfactory unraveled representation of the topography demands a sophisticated design for 3D consistency and least distortion.

Figure 2B:
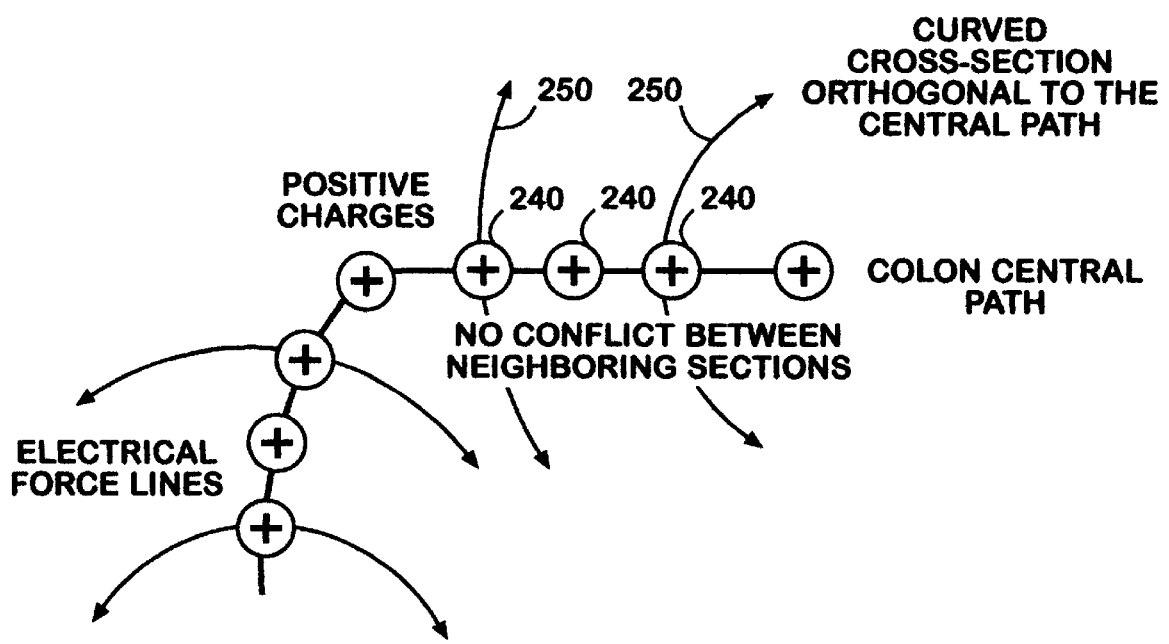
FIG. 2B displays the absence of conflict among cross sections generated via an electrical field model.

Electrical field theory serves as basis for a novel method that can consistently unfold any curvilinear tubular structure. As shown in FIG. 2B, suppose that positive charges 240 are distributed along the curvilinear central path, electrical force lines 250 are formed by the charged central path. At each point on the path, a curved cross-section can be defined with the electrical force lines from the point. Such curved surfaces fully fill in the 3D space, never conflict with each other, and are locally orthogonal to the central path. In particular, an image volume of a colon can be reformatted according to these curved cross-sections for unraveling. This is in marked contrast to the potential for neighboring conflict of planar cross sections as shown in FIG. 2A; neighboring planar cross sections 210 and 220 conflict at the intersections of the cross sections 230.

Figure 3A:
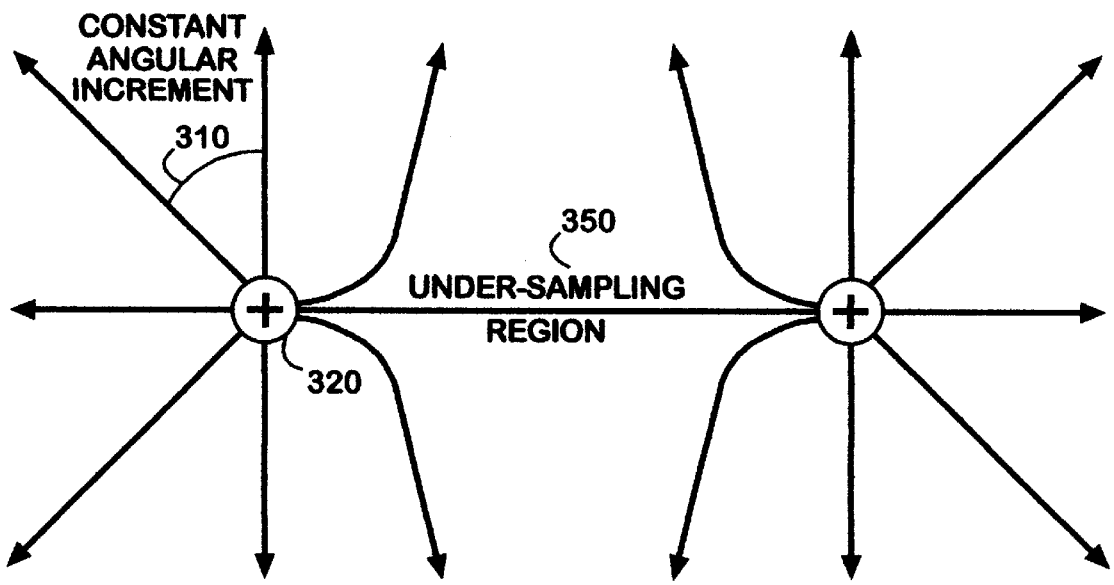
FIG. 3A depicts the potential under-sampling resulting from equi-angular sampling.
Figure 3B:
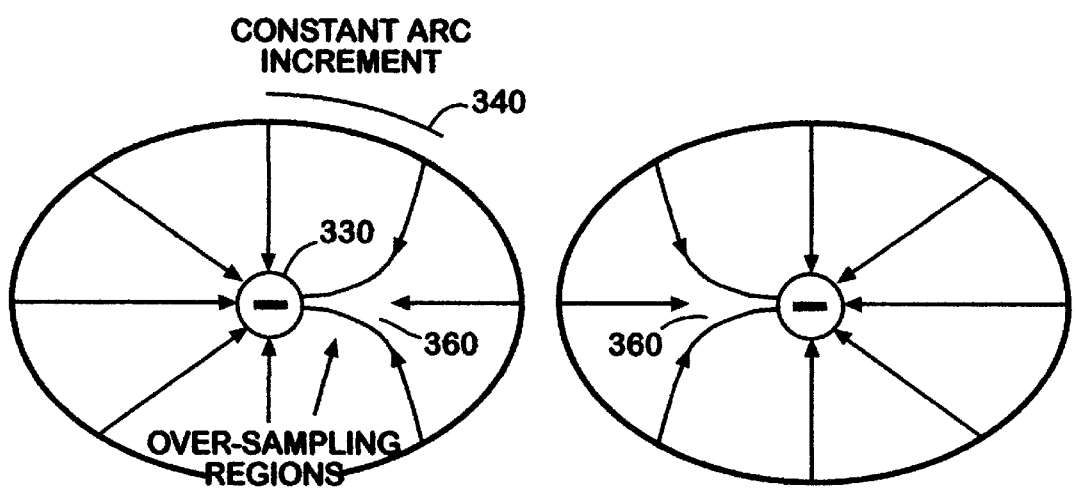
FIG. 3B depicts the potential over-sampling resulting from equi-arc sampling.

Discrete sampling is needed in reformation for a curved section. Two sampling schemes are equi-angular and equi-arc as depicted in FIGS. 3A and 3B respectively. In a preferred embodiment, equi-angular discrete sampling is used.

The equi-angular sampling is simpler. At any point on the colon central path 320, the local direction of the central path is cross-multiplied with a reference vector to generate a vector orthogonal to the local direction. The two orthogonal vectors are then cross-multiplied to form a vector orthogonal to both. The two orthogonal vectors thus generated can be used to define any direction that is orthogonal to the local direction of the central path. Along any direction orthogonal to the central path, a pre-specified radial sampling step 310 is made from the central path. Then, the local direction of the electrical force line is computed at this sampling position, and the next sampling step is made along the local direction. Typically, the total length for radial sampling is the same for all the curved sections.

The equi-arc sampling is based on the outcome of the equi-angular sampling. After the equi-angular sampling, each charge on the central path 330 is turned negative. From equidistant points on the boundary generated in the equi-angular sampling, radial sampling is done towards the central path. A constant arc distance 340 lies between each equidistant point on the boundary.

Computationally, the equi-angular sampling method is more efficient. However, the equi-arc method tends to produce equi-distant sampling points on the mucosal surface, which is generally a desirable feature. Either the equi-angular method or the equi-arc method may suffer from substantial geometric distortion due to under-sampling and over-sampling respectively. Distortion is more evident in regions where several segments of the colon central path are close. As a result, internal and external colon surfaces may be stretched or compressed in the unraveling process. FIG. 3 displays this potential distortion with respect to under-sampling 350 in equi-angular sampling in FIG. 3A and with respect to over-sampling 360 in equi-arc sampling in FIG. 3B.

Figure 4:
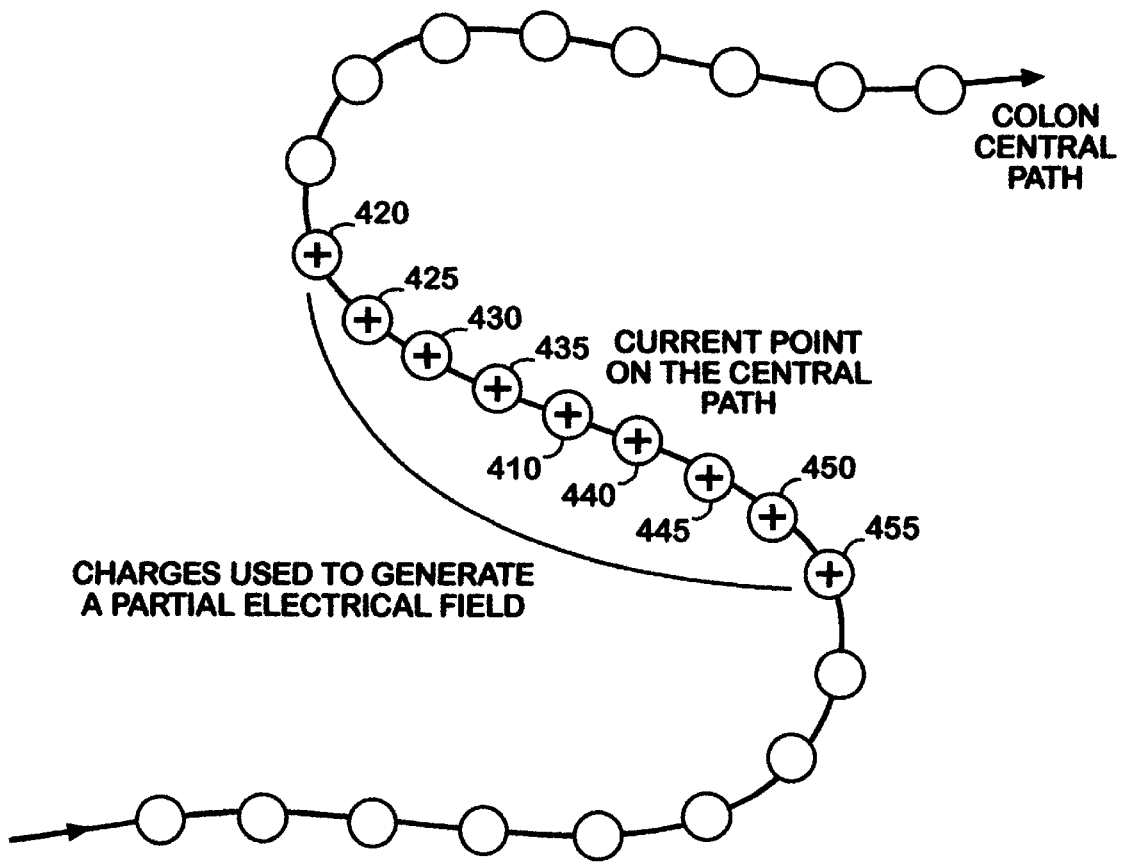
FIG. 4 displays a partial electrical field simulated along the central path.

To address this problem, as illustrated in FIG. 4, modifications can be made so that only charges 420–455 near a current point 410 on the central path are used to generate electrical force lines. The partial electrical field of this type allows more flexibility. If only one charge is used, planar cross-sections are generated, which may conflict; this results from the absence of other charges that would deflect the electrical force lines emanating from the charged current central path point. If all charges are involved, curved cross-sections are perfectly consistent, but distortion could be large. Generally, a satisfactory unraveling quality corresponds to an appropriate length of the charged colon central path segment that is dynamically centered at each current path point. The introduction of the partial electrical field also significantly reduces the computational time for unraveling.

After radial sampling is done for all cross-sections using either the equi-angular method or the equi-arc method, curved cross-sections are represented in polar coordinates. A cross-section can be opened by treating the polar coordinates of the section as Cartesian coordinates. All the opened cross-sections are then stacked to map the convoluted colon into a planar image volume, which can be surface/volume-rendered for various elongated displays.

In addition to directly flattening the colon with curved cross-sections as described above, we can also directly straightening the colon in a similar way. Although the field of view with a straightened colon is not as wide as a flattened counterpart, it is still much larger than that of a native convoluted colon rendering. In a particular embodiment, the present invention may be implemented as follows. The central path determination is accomplished using manually selected representative central path points. A cubic spline central path can be generated and resampled for equi-spatially distributed central path points. A rectangular grid is constructed through each resampling point and on the plane orthogonal to the colon central path. The rectangular grid points are mapped into polar coordinates. At each colon central path point, two perpendicular vectors are formed that are orthogonal to the local direction of the central path. The radial electrical force lines that correspond to the rectangular grid points are initially in the perpendicular plane but soon deflected by neighboring simulated electric charges. The effect a point charge will have on a spatial point is inversely proportional to the square of the distance between them. More generally, the field should be regarded as an inverse square field; in other words, a gravity field would be as valid as the electrical field model utilized. Each radial line point is then mapped onto the slice grid to produce a series of straightened images.

The following provide additional details for accomplishing the above described cross-section formation.

(1) For each point on the central path, find two orthogonal vectors perpendicular to the local central path direction by
   (a) taking the cross product of a reference vector and the local direction and normalizing the result to get Tx, Ty, and Tz which represent the normalized vector components of the first orthogonal vector.
   (b) taking the cross product of the T vector with the local direction and normalizing the results to get Sx, Sy, and Sz which represent the normalized vector components of the second orthogonal vector.

(2) Set up a rectangular grid for each central path point. For each grid point $(x_i, y_j)$, find its polar coordinates $(\rho_{ij}, \theta_{ij})$ as measured from the central path point.

(3) For each point in polar coordinates $(\rho_{ij}, \theta_{ij})$, the unit vector pointing to it in the orthogonal plane can be given by:

$$TSx = Tx \cdot \cos(\theta_{ij}) + Sx \cdot \sin(\theta_{ij})$$

$$TSy = Ty \cdot \cos(\theta_{ij}) + Sy \cdot \sin(\theta_{ij})$$

$$TSz = Tz \cdot \cos(\theta_{ij}) + Sz \cdot \sin(\theta_{ij})$$

(4) To generate a curved radial line of length $\rho_{ij}$ that is affected by an electric field, set the step size to the slice grid size (Vsize). Calculate the number steps of this size required to cover a length of $\rho_{ij}$ by taking Irad=Floor($\rho_{ij}$/Vsize). Conduct a ray extension loop Irad times, each time extending the X, Y, and Z vectors according to the following equations:

$$XTS(Ir) = XTS(Ir-1) + Vsize \cdot Dx$$

$$YTS(Ir) = YTS(Ir-1) + Vsize \cdot Dy$$

$$ZTS(Ir) = ZTS(Ir-1) + Vsize \, Dz$$

where Dx, Dy, and Dz are dependent on the local electric field.

(5) To calculate the electric field force on any point, create a charge index (Ipp) for central path points which ranges from (Ip−L) (the current point minus the electric field length) to (Ip+L) (the current point plus the electric field length). Step through this region by a predefined step size (Sef). If Ipp is in the data volume, find the distance between it and the current radial point given by $$xx = XTS(Ir) - XP(Ipp)$$

$$yy = YTS(Ir) - YP(Ipp)$$

$$zz = ZTS(Ir) - ZP(Ipp)$$

Find the length of the vector (dd) from xx, yy, and zz and normalize xx, yy, and zz. Calculate the local field effect caused by this Ipp point:

$$Fx = Fx + xx/(dd * dd)$$

$$Fy = Fy + yy/(dd * dd)$$

$$Fz = Fz + zz/(dd * dd)$$

Set Dx=Fx, Dy=Fy, Dz=Fz and use these D variables for the equation given in (4). Reset Fx, Fy, and Fz to zero for each new radial point.

Figure 5:
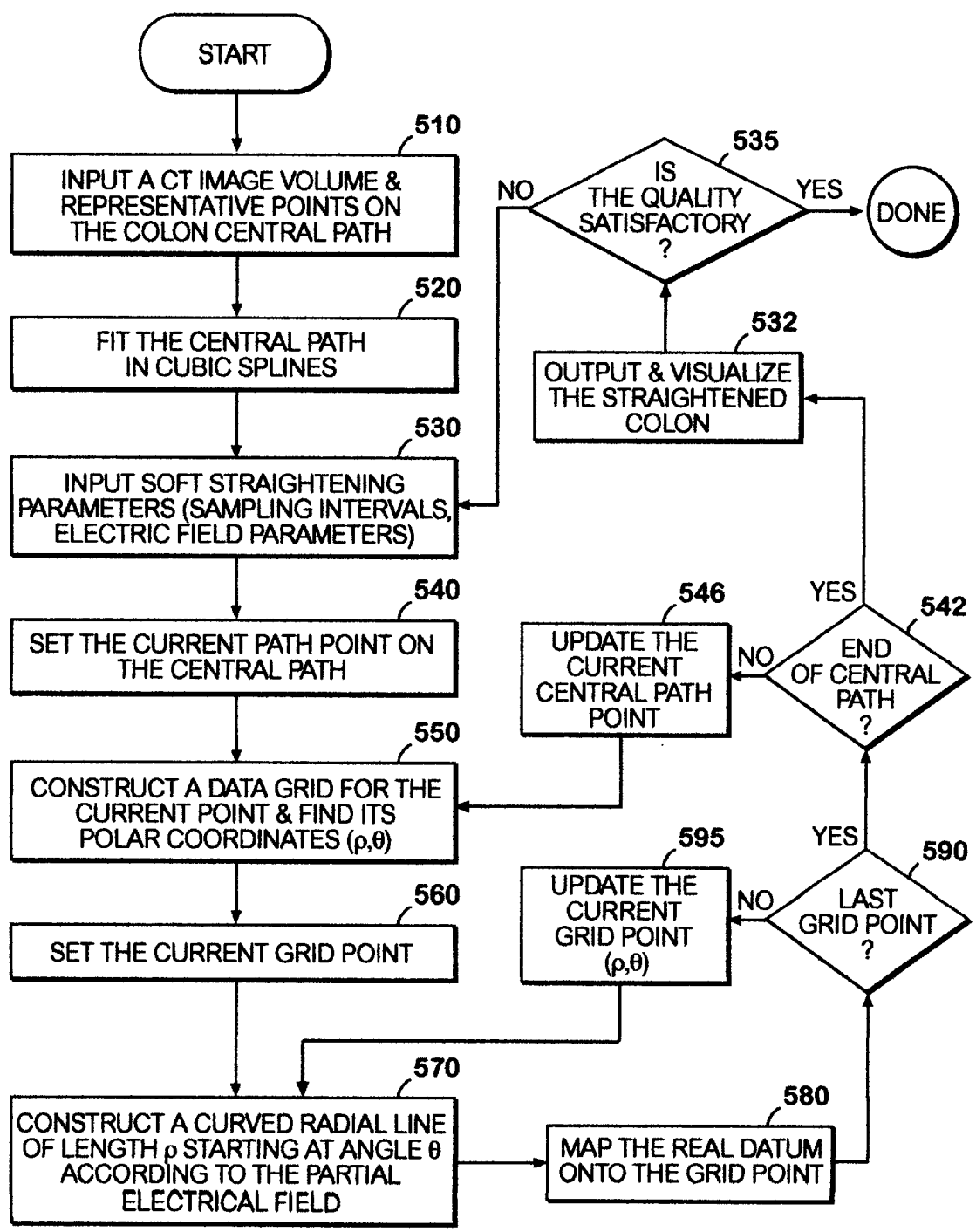
FIG. 5 is a flow chart of the straightening process according to the present invention.

This complete procedure is seen graphically in the flow-chart in FIG. 5. In step 510 and 520, central path determination is accomplished. First, a CT image volume and representative points along the central path are inputted in step 510. The representative points may be manually, semi-automatically or automatically determined. In step 520, a cubic spline central path can be generated and resampled for equi-spatially distributed central path points. Soft straightening parameters such as sampling intervals and electrical field parameters are entered in step 530.

Cross section formation occurs in steps 540–595. The formation of individual cross sections associated with each central point path occurs in steps 550–595. In step 540 the current path point is initialized to either the initial point in the central path or the initial point in the portion of the central path selected for unraveling. In step 550, a data grid is constructed for the current point. This rectangular grid is mapped into polar coordinates. The current grid point is initialized in step 560. In step 570, a curved radial line is generated according to the partial electrical field as described in step (4) above. In step 580, the real datum is mapped onto the grid point. Step 590 determines whether radial lines have been generated for all grid points in the current cross section. If radial lines have not been generated for all grid points in the current cross section, the next grid point is selected as the current grid point in step 595 and construction of the current cross section continues with step 570. If all radial lines have been generated, a further determination in step 542 is made as to whether cross sections have been generated with respect to all central path points considered. If all cross sections have not been generated, the current path point is advanced to the next central path point to be considered in step 546 and cross section generation for this path point is begun at step 550. If all cross sections have been generated, the straightened GI tract is outputted for visualization in step 532. If the quality of the output is not satisfactory in step 535, cross section reconstruction may be performed using different input parameters entered at step 530. After which, cross section formation 540–595 is repeated utilizing the new parameters. With a built-in checking mechanism to be described below and parameters well tuned in representative trials, this type of repetition should not be often needed.

In the straightening/flattening process, generally speaking, pixel centers on either curved or planar cross-sections are not coincident with centers of original image voxels. As a result, interpolation is needed to assign a gray level to each pixel of a cross-section. Nearest neighbor interpolation and tri-linear interpolation are the most widely used interpolation methods. The first interpolation method simply uses the value of the voxel nearest to a point of interest. The second interpolation method computes the value at a point using the values from its eight neighbors. Tri-linear interpolation is used in the preferred embodiment of the present invention, which produces substantially better image quality Impact of Varying Partial Electric Field Size As previously described, simulating a complete electrical field is both computationally expensive and may lead to geometric distortions. As a preliminary study, the following experiment was performed to evaluate the impact of partial electrical field size upon computational efficiency of soft straightening and geometric distortion. A colonoscopy phantom (Training Model I-B, Koken Co., Ltd, Tokyo, Japan) was chosen for analysis. The phantom colon was scanned with CT. It was determined that the average Hounsfield Unit (HU) value of its wall was approximately 180. Artificial polyps of approximately the same HU were constructed with 1% and 2% Hypaque solutions contained in the fingertips of latex gloves. Small polyps (less than 1 cm in diameter) used the 2% solution and the larger polyps used the 1% solution. The tips were tied off in varying sizes using 8-pound test fishing line. With the polyps and colon wall of similar density, polyp detection was a function of geometry and not contrast differences. Four artificial polyps of ranging from 0.48 $cm^3$ to 2.03 $cm^3$ were chosen and placed in the upper left quadrant of the phantom colon (left transverse colon and superior region of descending colon) in varying positions by dropping them in the rectal orifice and allowing them to settle in random spots in the limited region. They rested on the posterior surface of the colon wall between haustra when the phantom was positioned in a supine position.

The colon phantom containing the four polyps was scanned with a spiral CT scanner with the following scan parameters: (mas=150, kvp=120, collimation (mm)=5, table speed (mm/sec)=5, reconstruction interval (mm)=1). The data was cropped to the desired area, converted from 16-bit to 8-bit representation, and re-mapped to 256 gray levels.

A series of 27 points progressing from the distal portion of the descending colon to the median transverse colon represented the central path of the colon in the desired region. The data set was transferred to a Dell OptiPlex Pentium II 333 MHz computer running IDL (Interactive Data Language from Research Systems, Boulder, Colo., USA), the programming language used to implement soft straightening in this preferred embodiment. Central path determination was performed using the 27 preliminary points and cubic spline interpolation to yield 285 central path points.

For each point, a grid is constructed in rectangular coordinates to hold the slice data. This rectangular grid is re-mapped into polar coordinates around each central point. At each point, two perpendicular vectors are found to the local direction of the central path. For hard straightening, radial lines are extended out from the central point (acting as a single point charge) in the perpendicular plane and mapped to the slice grid. For soft straightening, the radial lines start in the perpendicular plane but deflect due to the influence of neighboring simulated electric charges. The effect a point charge will have on the radial line is inversely proportional to the square of the distance between them. Each radial line is then re-mapped onto the slice grid to produce a series of straightened images.

As stated earlier, it is possible to create point charges at all points of the central path and let their electric fields interact to produce slices with no intersections. To reduce both geometric distortion and computation time, a partial electric field that extends a small length (L) on each side of the current central path point is used. Each current central path point is always modeled as a point charge. To examine the effect of a variety of partial electric field lengths, four straightening trials were performed.

The first trial was run with L=0. The current central path point acted as a point charge, but zero neighboring point charges were present. Thus, the planar section generated at the current point was not influenced by neighboring point charges, so each slice was planar, the same result as done with hard straightening. Three other trials were done with L=9, L=15, and L=21. These trials had 9, 15, and 21 point charges respectively on each side of the current central path point. The program stepped through this local electrical field with a step size of 3 so every third point charge in the current electrical field length affected the current slice. This effectively created an inter-charge distance of three. The straightening program generated a series of 285 images and stacked them into a straightened colon.

These slices were stepped through in an animated fashion to produce a movie effect. The straightening program also marked the location of certain planes in the original data so slices could be visualized and compared on the real data.

Due to the computing time needed for the L=21 field size, this trial was run on a smaller portion of the data. The outputs for the various straightening trials were analyzed for distortion and problems with region misrepresentation. The original volume with the planes digitally inserted was inspected to study the plane orientations.

As a final test, straightening was done on patient CT data. Two tests were run on a small region showing a polyp near a sharp bend. For this data, 9 representative points were picked in a distal to proximal direction and interpolated to a fit of 65 points. Straightening was done with field sizes of L=0 and L=21, and the results were analyzed as described before.

Figure 6A:
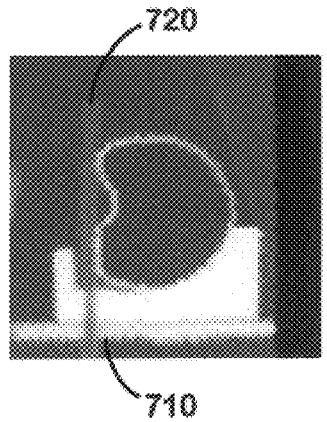
FIG. 6A depicts the distortion seen in a trial of the phantom data set with electric field length parameter L=0.
Figure 6B:
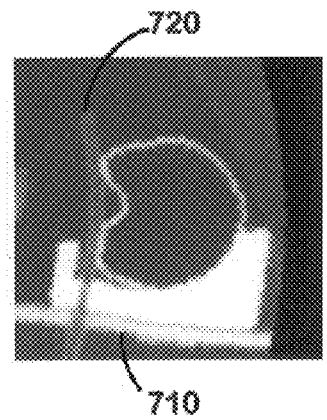
FIG. 6B depicts the distortion seen in a trial of the phantom data set with electric field length parameter L=9.
Figure 6C:
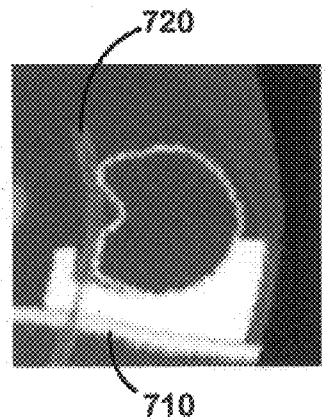
FIG. 6C depicts the distortion seen in a trial of the phantom data set with electric field length parameter L=15.

Representative sagittal reconstructions of the phantom and the corresponding planes of the numbered axial cuts illustrate the results of this experiment. FIG. 6 depicts the distortion seen in three trials on the phantom data set at the $44^{th}$ of the 285 central path points. For hard straightening (electric field length (L) equals zero) shown in FIG. 6A, there is no visible distortion; the base plate 710 and the plastic rod 720 used to hold the colon in place appear flat and at right angles to each other. As the electric field length increases to L=9 and L=15, FIGS. 6B and 6C respectively, the base plate and plastic rod show progressively more bending distortion.

Representative data for hard straightening (L=0) can be seen in FIG. 7. The illustrated data focuses on a polyp 810 that was counted three times due to a kink in the central path. The kink causes the first group of slices (as depicted by slice 238) to intersect the polyp 810, and then alternating regions (as depicted by the other slices) do not to intersect it, giving the appearance that three polyps were counted. The numbers 238, 251, 260, 265, 274 are the slice numbers along the 285 point central path represented by FIGS. 7B–7F respectively. FIG. 7A displays the orientation of 5 slices and the central path as seen in a sagittal plane of the original volume. FIGS. 7B–7F display the views at the 5 selected slices. The polyp 810 appears to be counted three times.

Representative data for soft straightening with L=9 can be seen in FIG. 8. The images focus on the same area and same slices as with hard straightening seen in FIG. 7, but the polyp 810 is now counted twice. The regions after slice 260 that had intersected the polyp with hard straightening (L=0) no longer intersect it. A comparison of the images from FIG. 7 with L=0 shows that the slices do not cross each other as often when the small electric field (L=9) is used. The numbers 238, 251, 260, 265, 274 are the slice numbers along the 285 point central path represented by FIGS. 8B–8F respectively. FIG. 8A displays the orientation of 5 slices and the central path as seen in a sagittal plane of the original volume as seen along the central path. FIGS. 8B–8F display the views at the 5 selected slices. The polyp 810 appears to be counted two times as it disappears between slice 238 (FIG. 8B) and slice 260 (FIG. 8D).

FIG. 9 shows representative data for soft straightening with L=15. The images focus on the same area and same slices as FIGS. 7 and 8, but the polyp 810 is now counted once; it is seen continuously from slices 238 (FIG. 9B) to slice 260 (FIG. 9D), but it permanently disappears after slice 260. Thus, the intervening region between slices 238 and 260 that did not show the polyp with L=9, as seen in FIG. 8, now intersects the polyp. A comparison of the images from L=0 and L=9 shows that the slices do not cross each other as often when L=15. With L=15, only slice 238 crosses any of the other slices as seen in FIG. 9A.

Table 1 below illustrates the computing time required for each straightening trial on the colon phantom. The trials for L=0, L=9, and L=15 were run on a path of 285 points, and took approximately one hour, three hours, and six hours respectively. The trial with L=21 was run on a central path of 131 points but still took approximately 6 hours.

TABLE 1

Computing Times for Each Trial on the Phantom Colon

| Number of Involved Charges | Number of Interpolated Path Points | Computer Time (Hour) |
|---|---|---|
| 1 | 285 | 1 |
| 9 | 285 | 3 |
| 15 | 285 | 6 |
| 21 | 131 | 6 |

Figure 11A:
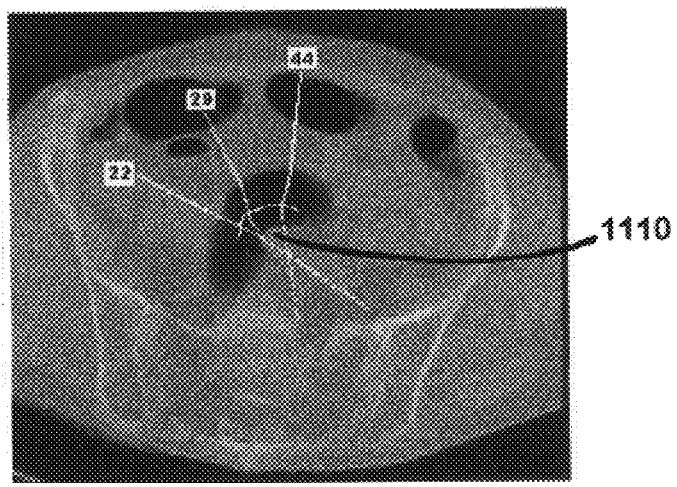
FIG. 11A illustrates an image of an actual patient data set showing a polyp 1110 near a bend being counted twice using soft straightening (electric field length parameter L=21).
Figures 11B, 11C, 11D:
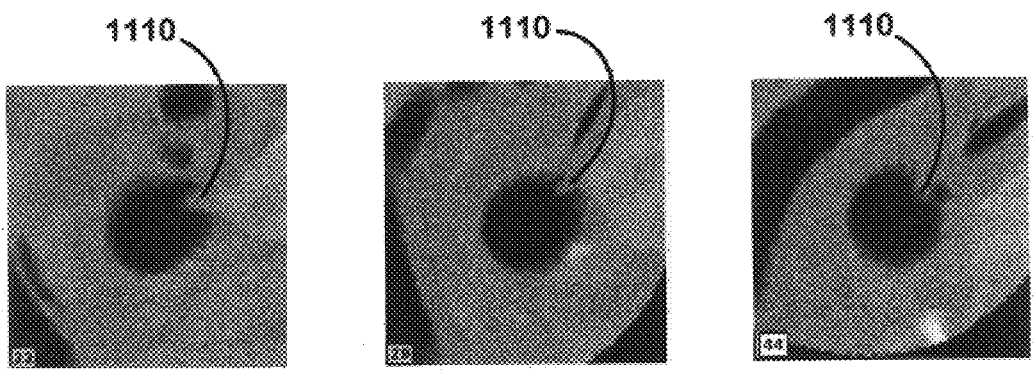
FIGS. 11B–11D display the views at 3 selected slices through central path points 22, 29 and 44 as shown in FIG. 11A with electric field length parameter L=21, respectively.

The final data is obtained from two straightening trials (L=0 and L=21) on human CT data. FIG. 10 illustrates a polyp 1110 near a bend being counted twice using hard straightening (L=0). Three representative slices are illustrated in FIGS. 10B, 10C and 10D corresponding to slices through central path points 22, 29 and 44 respectively. FIG. 11 illustrates the results with soft straightening on real data using L=21. The polyp 1110 now appears once even though it is quite distorted in slice 29, FIG. 11C. A comparison of FIGS. 11A and 10A demonstrates more even sampling of the outer curve with curved sections.

FIGS. 12 and 13 further illustrate the phantom experiment and the patient study respectively. FIG. 12A illustrates a surface rendering of the colon phantom. FIG. 12B illustrates a surface rendering of a segment showing a polyp. FIG. 12C depicts the segment soft-straightened using nearest neighbor interpolation. FIG. 12D depicts the same segment soft-straightened using tri-linear interpolation. FIG. 13A illustrates a surface rendering of the colon viewed from left. FIG. 13B illustrates a surface rendering of opened sigmoid showing a polyp, the cutting plane indicated by the black line in FIG. 13A. FIG. 13C depicts the sigmoid segment soft-straightened using nearest-neighbor interpolation while FIG. 13D depicts the same segment soft-straightened using tri-linear interpolation.

Figure 12A:
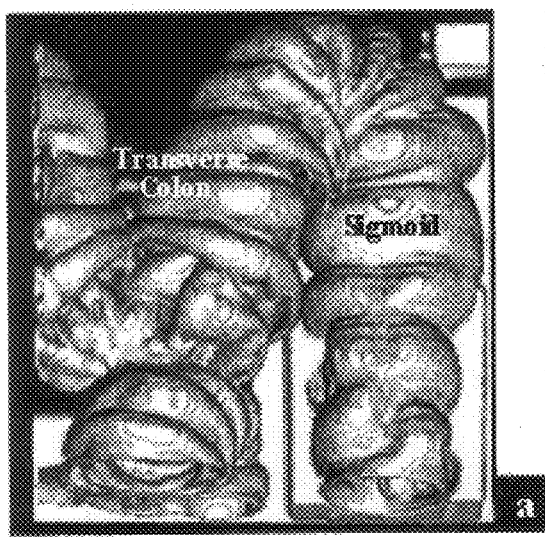
FIG. 12A illustrates a surface rendering of the colon phantom.
Figure 12B:
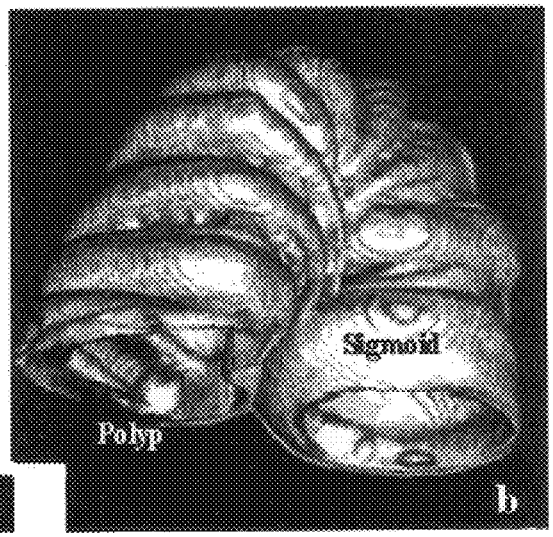
FIG. 12B illustrates a surface rendering of a segment showing a polyp.
Figure 12C:
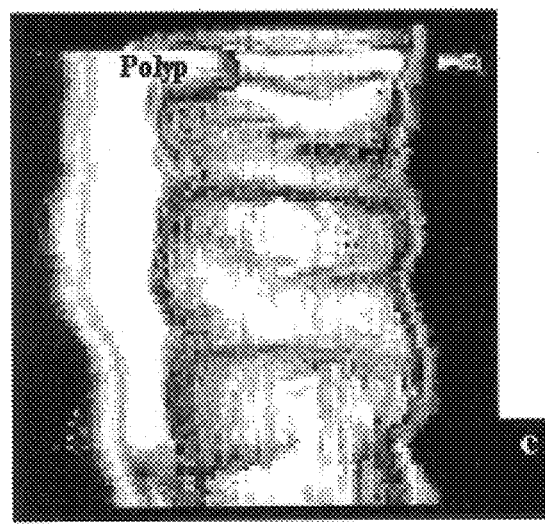
FIG. 12C depicts the segment of FIG. 12B soft-straightened using nearest neighbor interpolation.
Figure 12D:
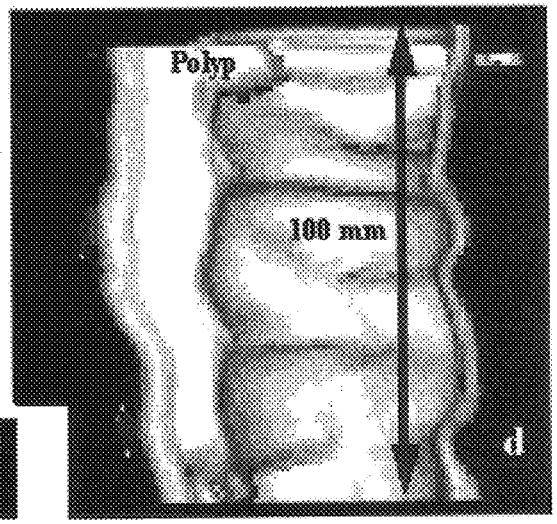
FIG. 12D depicts the segment of FIG. 12B soft-straightened using tri-linear interpolation.
Figure 13A:
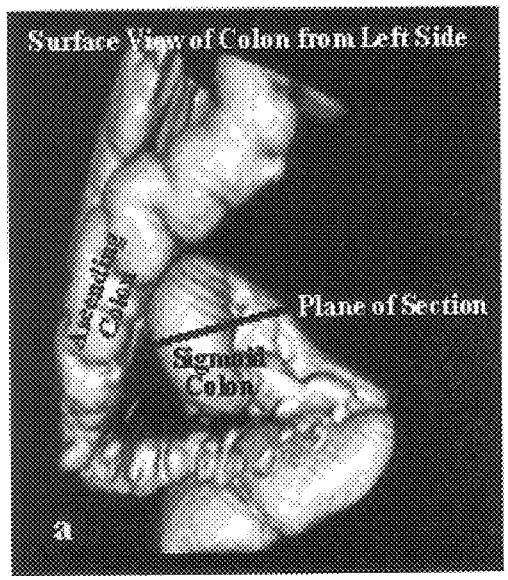
FIG. 13A illustrates a surface rendering of the colon viewed from left.
Figure 13B:
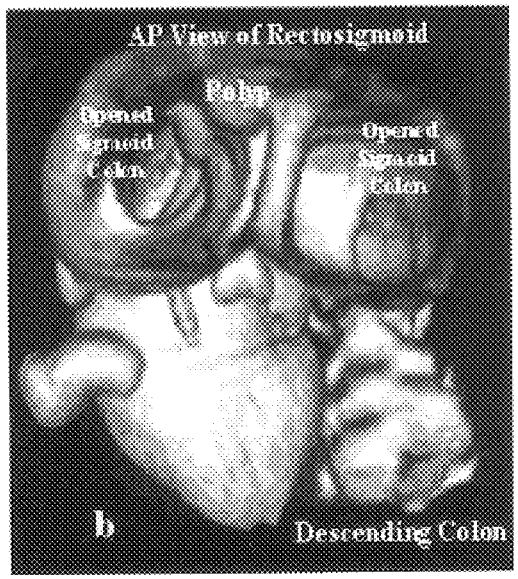
FIG. 13B illustrates a surface rendering of opened sigmoid showing a polyp, the cutting plane indicated by the black line in FIG. 13A.
Figure 13C:
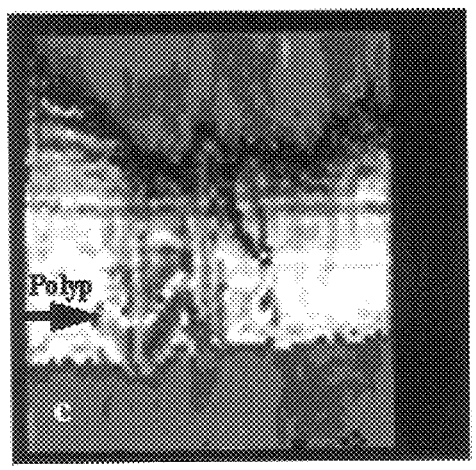
FIG. 13C depicts the sigmoid segment of FIG. 13B soft-straightened using nearest-neighbor interpolation.
Figure 13D:
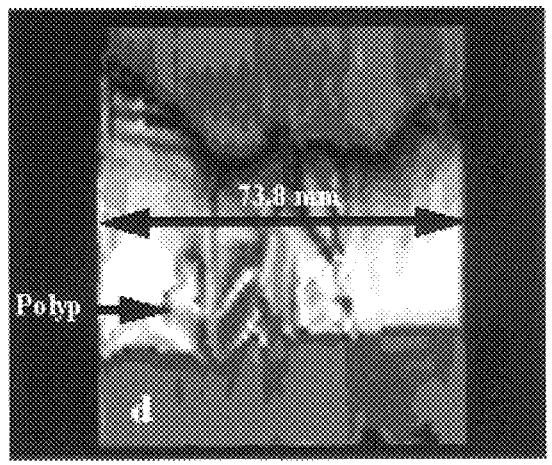
FIG. 13D depicts the segment of FIG. 13B soft-straightened using tri-linear interpolation.

These figures, further, show the difference between the nearest neighbor interpolation and tri-linear interpolation methods in terms of rendering quality. It can be easily seen that the nearest neighbor interpolation method (FIGS. 12C and 13C) led to significantly stronger noise and much worse visualization than that exhibited by the tri-linear interpolation method (FIG. 12D and 13D).

The trials with real CT data illustrate the expected cause of double counting, a sharp turn with the polyp located on the inner portion of the turn. These results indicate that hard straightening is subject to multiple counting and uneven slice distribution in the outer portion of curves. Multiple polyp counts were illustrated most clearly with the phantom colon while the human CT trials more clearly demonstrated the sampling problems on the outer portion of curves. Soft straightening solves these problems but it introduces distortion to the images; however, this distortion does not greatly affect the conspicuity of polyps.

Soft straightening relies on the principle that electric field lines cannot cross, yet the soft straightening trials show that some cross sections intersect. The main reason is that the charged central path segment in a particular region may not be long enough to affect all slices that cause intersections. As stated earlier, if the all points on the central path were modeled as point charges, there would be no slice intersections, since the resultant electrical field must be consistent. A partial electric field though is active in only a small region surrounding the current central path point. Because of the temporary nature of the electric field region, some intersections were still possible.

However, as the length of the charged central path segment increases, the chance of slice intersection decreases, and such intersections are pushed away from the colon central path, as shown in FIGS. 7–12. For example, a number of intersections were generated in the phantom experiment with hard straightening (L=0, FIG. 7), while only slice 238 intersects the other slices in the same experiment with soft straightening (L=15, FIG. 9). Also, in the patient study with hard-straightening (L=0, FIG. 10) slices 22 and 44 intersect at the surface of the polyp 1110, while with soft straightening (L=21, FIG. 11) these slices intersect only when they are outside the colon wall.

Improving the Speed of Soft-straightening

Even with the improved speed of utilizing a partial rather than a complete electrical field, the soft-straightening algorithm as directly implemented is extremely time-consuming because several loops are needed to track electrical force lines from each colon path point and along every direction. The computational efficiency of the system according to the present invention can be improved by tracing only representative electrical force lines and additional force lines are generated via interpolation. This method improves computational speeds by up to approximately forty times while maintaining clinically useful quality.

As with the original soft-straightening approach, the first task is central path determination and fitting. The central path determination may be accomplished semi-automatically using an IDL program to determine the central path in an image volume; this central path determination method fits a GI tract central path through a sequence of user selected intraluminal points using cubic spline interpolation. GI tract tracking follows the fitted central path. The performance improvement of this embodiment occurs during cross-section formation.

The major portion of computation in the direct implementation of electrical field based GI tract straightening is for tracking electrical force lines from each central path point and along every direction in the cross-section. This demands estimation of the local direction of the electrical force line at every pixel of all the cross-sections locally orthogonal to the central path, and involves synthesis of the resultant force from multiple charges. The following modified process for soft straightening of the GI tract reduces this computational cost:

(1) Charge the colon path

Positive point charges are placed on the central path with an inter-charge distance m. The electrical force $\vec{f}$ due to a positive point charge has the magnitude $$|\vec{f}| = \frac{1}{kd^2}$$

where d is the distance from the charge to a spatial point of interest, and k is introduced to control the strength of the force.

(2) Select and track representative electrical force lines

Figure 14:
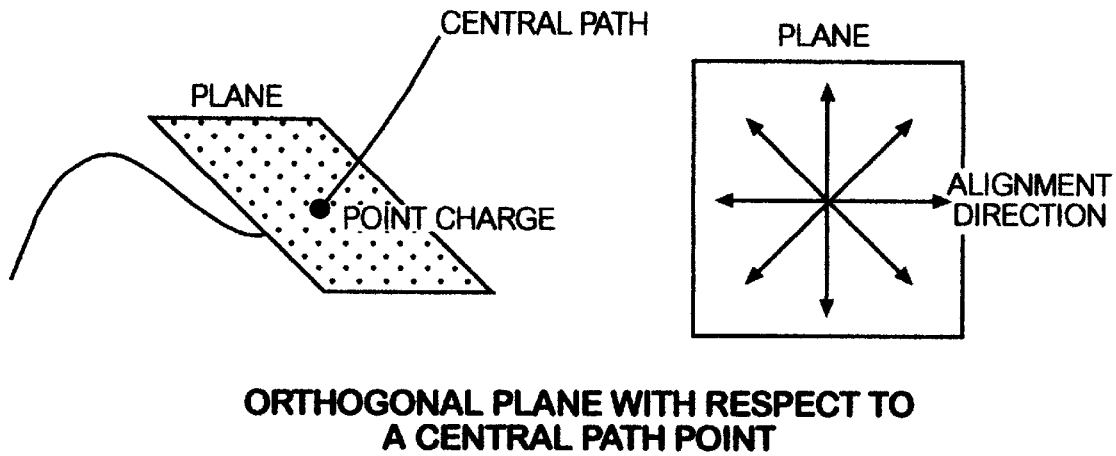
FIG. 14A depicts the creation of an orthogonal plane through a central path point.
FIG. 14B depicts the orthogonal plane of FIG. 14A with 8 electrical force lines through the central path point.
Figure 15:
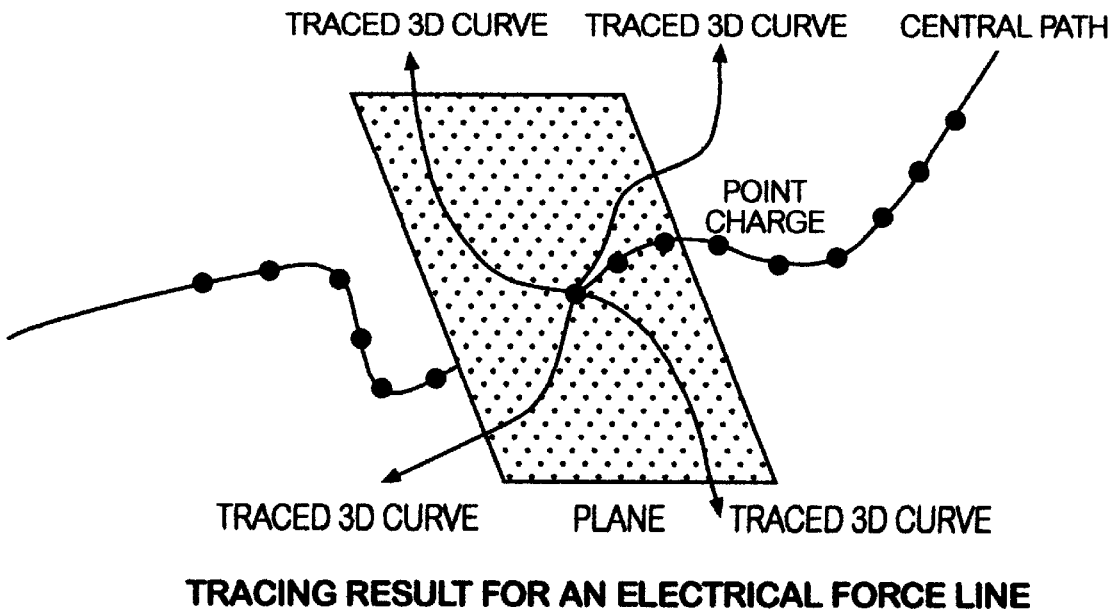
FIG. 15 shows the deflection of a traced electrical force line from the orthogonal plane as other neighboring charges act upon it.

For each cross-section, K representative electrical force lines are specified for direct tracking, where K is a small number, such as 8 in a preferred embodiment. In the orthogonal plane through each central path point of interest, K directions are equiangularly defined from the central path point as illustrated in FIG. 14. Direction 0 is referred to as the reference direction. Tracking of the electrical force lines starts from the current path point along each initially defined direction. The electrical lines initially stay within the plane, then are deflected away from the plane by neighboring charges, and trace a smooth 3D curved cross-section as seen in FIG. 15. Either a complete electrical field or a partial field can be assumed. In a partial field based implementation, only 2L+1 charges are used that are close to the current path point to reduce tracking time.

(3) Form curved cross-sections

Figure 16:
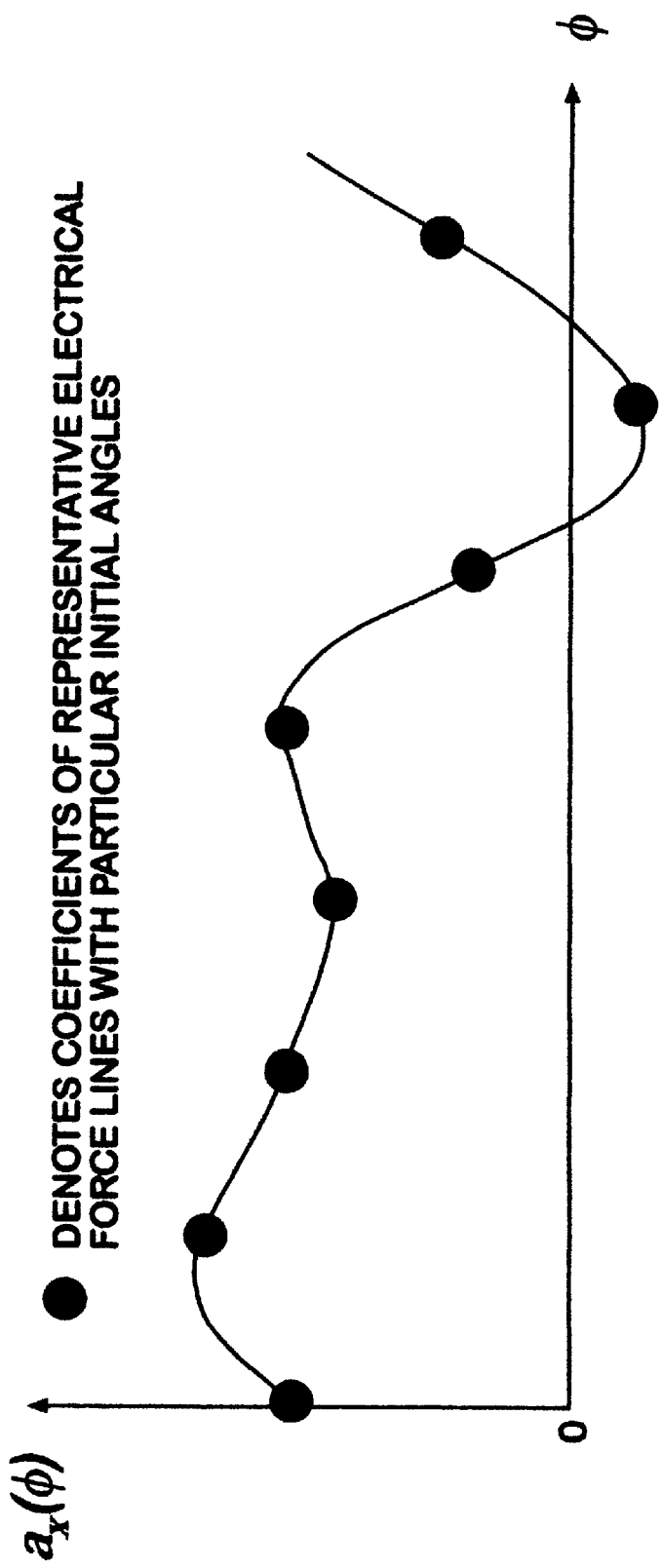
FIG. 16 depicts an example coefficient determination via interpolation.

After the representative electrical force lines are obtained for each cross-section, an electrical line starting in an arbitrary initial direction, $\phi$, relative to the reference direction can be interpolated. The electrical force lines can be modeled as quadratic polynomial curves in a parametric form using the following formulas:

$$x = a_x(\phi) * l^2 + b_x(\phi) * l + x_0$$
$$y = a_y(\phi) * l^2 + b_y(\phi) * l + y_0$$
$$z = a_z(\phi) * l^2 + b_z(\phi) * l + z_0$$

where (x,y,z) denotes a point on the line, l is the distance from the point (x,y,z) to the current path point $(x_0, y_0, z_0)$, and the coefficients of the polynomials for the representative force lines can be directly found from tracked data. Then, the coefficients of the polynomial for a force line at any initial angle $\phi$ can be interpolated such as seen in FIG. 16, and a curved cross-section can be formed.

(4) Map curved cross-sections onto corresponding rectangular grids and straighten the GI tract.

Curved cross-sections must be mapped onto corresponding rectangular grids to straighten the GI tract. Since each curved cross-section contains numerous curved electrical force lines originating from a central path point, it is natural to define polar coordinates according to these force lines, and then transform the polar coordinates into Cartesian ones for a planar version of the cross-section. Finally, these cross-sections are stacked to straighten the colon.

Figure 17:
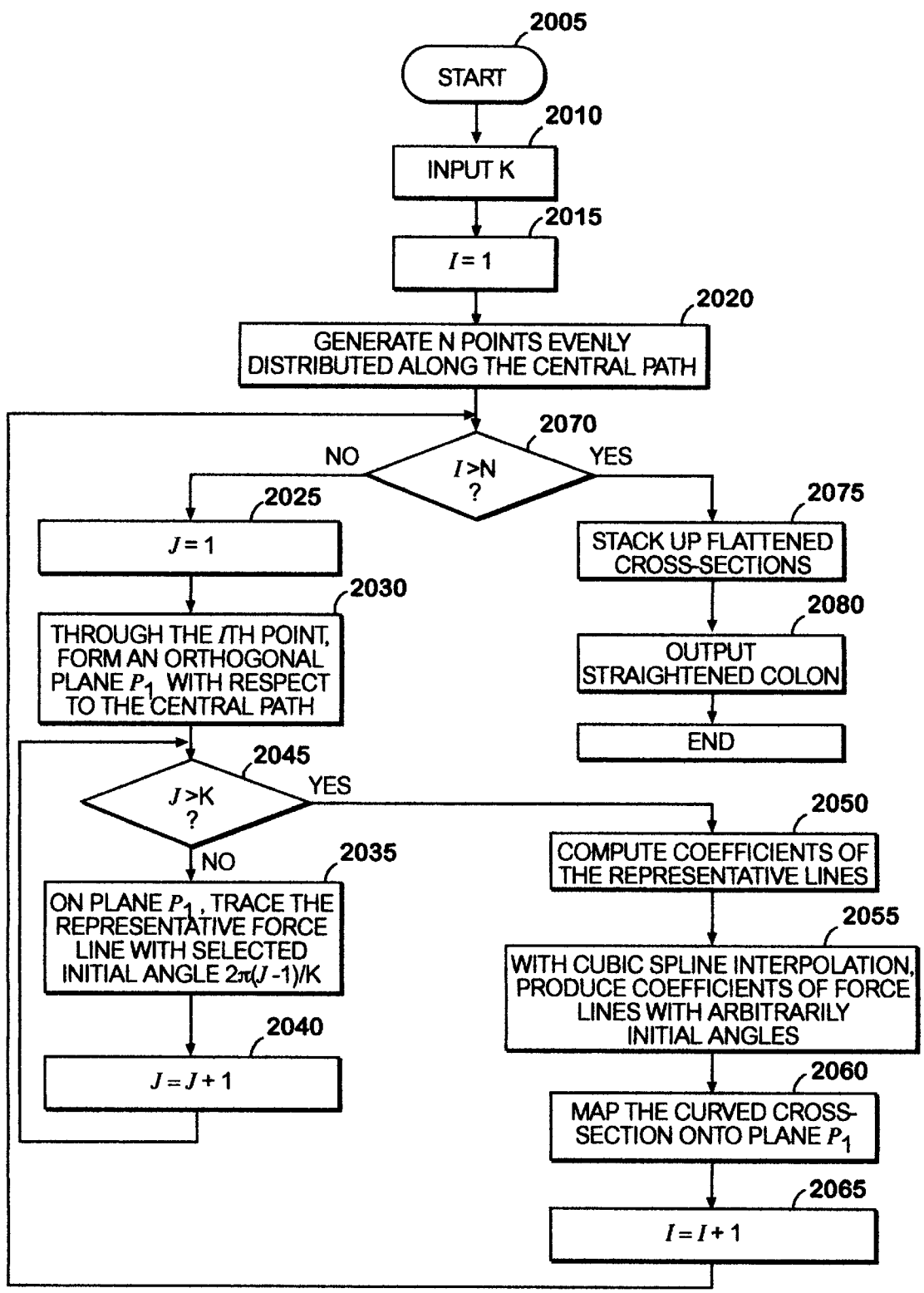
FIG. 17 is a flowchart of the accelerated straightening method according to the present invention.
Figure 18A:
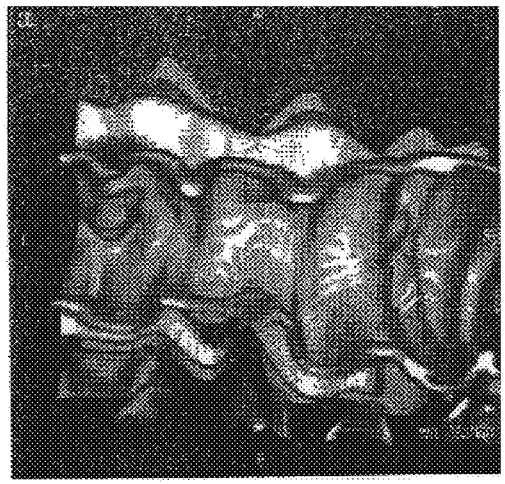
FIGS. 18A–18D depict a straightened colon phantom using the force line interpolation approach: (A) shows the internal view after splitting the colon; (B) shows the internal view from one end; and (C) and (D) show planar slices at polyps.
Figure 18B:
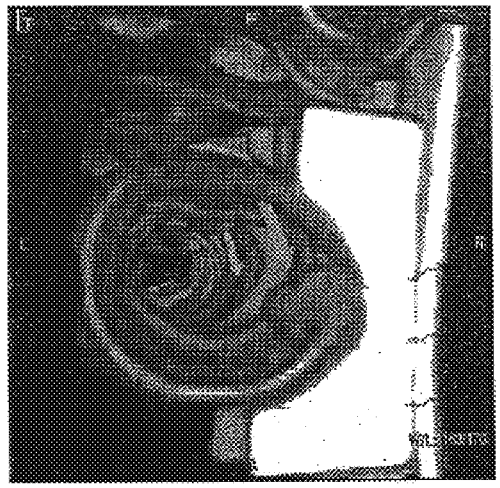
Figure 18C:
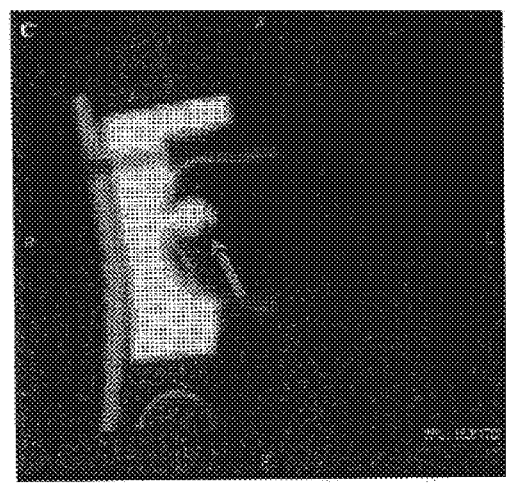
Figure 18D:
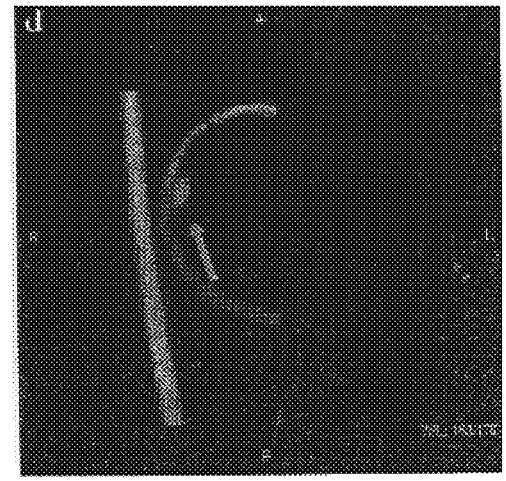
Figure 19A:
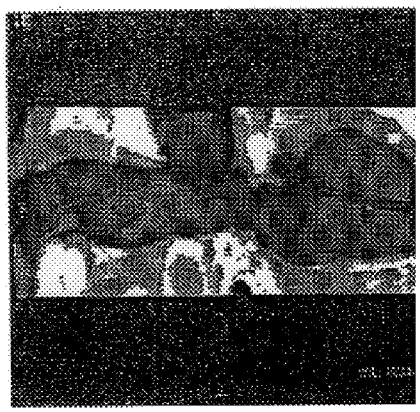
FIGS. 19A–19F depict a straightened patient colon using the force line interpolation approach: (A) shows the internal view after splitting the colon; (B) shows the internal view from one end; (C)–(E) show close-ups of polyps, respectively; and (F) is a coronal view showing one polyp.
Figure 19B:
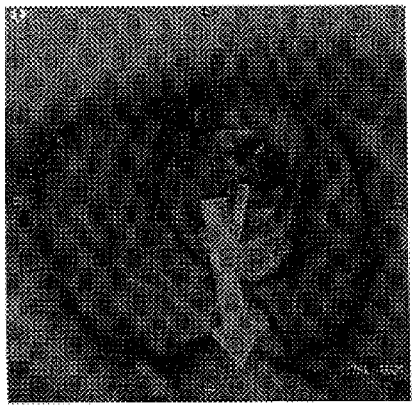
Figure 19C:
Figure 19D:
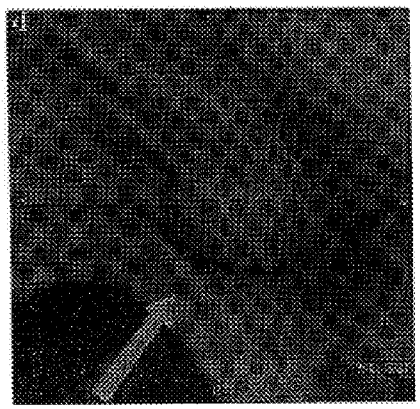
Figure 19E:
Figure 19F:

This accelerated soft straightening approach is illustrated graphically in the flowchart in FIG. 17. This flowchart only covers the cross-section formation portion of the overall straightening process. At the start, step 2005, of the flow chart, central path determination and fitting have already occurred. Further, standard soft-straightening parameters such as sampling intervals and electric field parameters have already been set. In step 2010, parameter K is set, which is the number of representative force line for each cross section. Then, N is generated via interpolation, which is the number of curved cross-sections to be formed along the central path in step 2020. In step 2015, counter I is initialized to 1. At this point, cross section formation begins. For each of the N points a curved cross-section is generated, representative force lines are traced in steps 2025–2045, additional force lines are generated via interpolation in steps 2050 and 2055 and the curved cross-section is mapped onto the corresponding rectangular grid in step 2060. Steps 2015, 2065 and 2070 provide the initialize, condition check and counter mechanics for incrementally proceeding through each of the N central path points.

At each central path point of interest a curved cross-section is generated. First, an orthogonal plane is formed in step 2030 as shown in FIG. 14. K representative electrical force lines are traced equiangularly in steps 2035–2045 as illustrated in FIG. 15. Steps 2025, 2040 and 2045 provide the initialize, condition check and counter mechanics for incrementally proceeding through each of the K representative force lines. Step 2035 traces each representative line. The functional fitting coefficients for these representative force lines are computed in step 2050. From the computed coefficients, coefficients for additional force lines can be generated using cubic spline interpolation in step 2055. Curved cross sections are then mapped onto associated orthogonal planes in step 2060.

In step 2075, the mapped cross-sections are stacked, and the straightened GI tract is outputted in step 2080.

A colonoscopy phantom colon (Training Model I-B, Koken Co., Ltd, Tokyo, Japan) and a patient were selected to demonstrate the feasibility of our fast soft-straightening algorithm based upon force line interpolation. Both of them were scanned with spiral CT. The data were compressed into 1 mm cubic 8 bit voxels. As a result, the phantom image consists of 156 by 156 by 186 voxels, and the patient image 256 by 256 by 197 voxels. The colon paths in the two cases were manually traced with the interactive interface of the Analyze™ (Biomedical Imaging Resource, Mayo Foundation, Rochester, Minn.). The data sets were transferred to a personal computer (Dell OptiPlex Gxa, 333 MHz, WinNT Workstation 4.0) for soft straightening. Both the direct tracing algorithm and the force line interpolation approaches were implemented in the programming language IDL (Research Systems, Boulder, Colo., USA).

FIG. 18 shows the results of the straightened colon phantom using the interpolation approach. To observe the interior surface of the straightened segment, the segment was split in half lengthwise. FIG. 18A shows the internal view after splitting the colon. FIG. 18B shows the internal view from one end. FIGS. 18C and 18D show planar slices at polyps.

FIG. 19 shows similar results obtained from the patient data. It is clear to see polyps from these views. FIG. 19A shows the internal view after splitting the colon. FIG. 19B shows the internal view from one end. FIGS. 19C, 19D and 19E show close-ups of polyps. FIG. 19F is a coronal view showing one polyp.

Table 2 lists the computer time spent in these cases.

TABLE 2

Time Comparison of Interpolation Method and Complete Tracing Method

| | Size of Partial Electric Field (number of charges) | Phantom Colon | Patient Colon |
|---|---|---|---|
| Interpolation | 9 | 4 min | 5 min |
| | 15 | 8 min | 10 min |
| Complete | 9 | 180 min | 200 min |
| Tracing | 15 | 360 min | 390 min |

Note that in the mapping stage of the fast algorithm, since the converted Cartesian coordinates typically are not integers, some interpolation methods should be used to determine gray values at these Cartesian coordinates. Commonly used tri-linear interpolation is applied here to produce satisfactory results as shown in FIGS. 18 and 19.

In practice, it is important to be certain that there are no conflicts among neighboring curved cross-sections, even a partial electrical field is used. Generally, it is complicated and time-consuming to check the conflicts of this type voxel-wise.

Figure 20A:
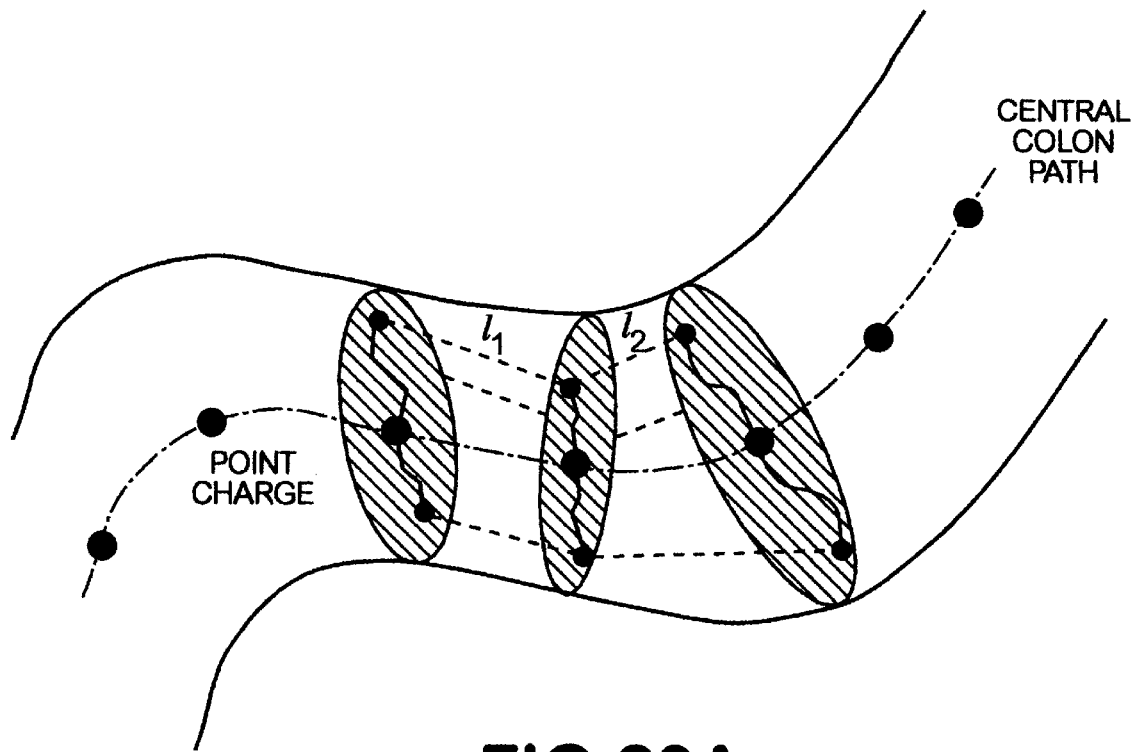
FIG. 20A depicts end-points of representative electrical force lines with potential conflict between adjacent cross-sections.
Figure 20B:
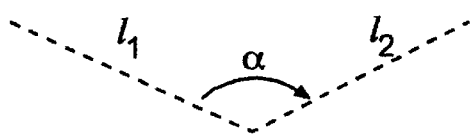
FIG. 20B shows the condition, $\alpha > 90°$ for all of the force lines, under which there is no conflict between the adjacent cross-sections as shown in FIG. 20A.
Figure 20C:
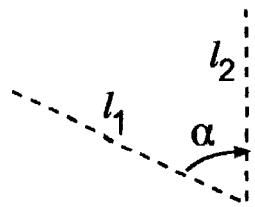
FIG. 20C shows the condition, $\alpha \leq 90°$ for all of the force lines, under which there is a conflict between the adjacent cross-sections as shown in FIG. 20A.

To address this problem, the following practical scheme has been devised. This scheme is illustrated in FIG. 20. The idea is that instead of checking voxel-by-voxel for conflicts between two adjacent cross-sections, examination only occurs if there are any conflicts between corresponding end points of representative electrical force lines. These electrical force lines are those that are directly traced, as described in step 2 of the fast straightening algorithm as seen in FIG. 20A.

For each representative force line, the end point is found, the distance from which to the current point on the central path is always a constant, which is the radius of the cross-section. The end points are then sequentially linked with peripheral vectors. Heuristically, the angle ox between successive vectors carries vital information on whether the corresponding force lines intersect or not. If $\alpha \leq 90°$, FIG. 20C, the assumption is made that there is a conflict between the neighboring cross-sections. If $\alpha > 90°$, for all of the force lines, FIG. 20B, the cross-sections are considered not interfere each other, and the norms of the peripheral vectors can be used to describe the spatial distortion of the straightening transform. Note that conflicts associated with a norm less than the minimum diameter of polyps of interest would not affect their detection. The total number of conflicts calculated this way provides an estimate of real conflicts. Such conflicts must be due to inappropriate selection of straightening parameters, and should be eliminated by adjusting these parameters.

Figure 21A:
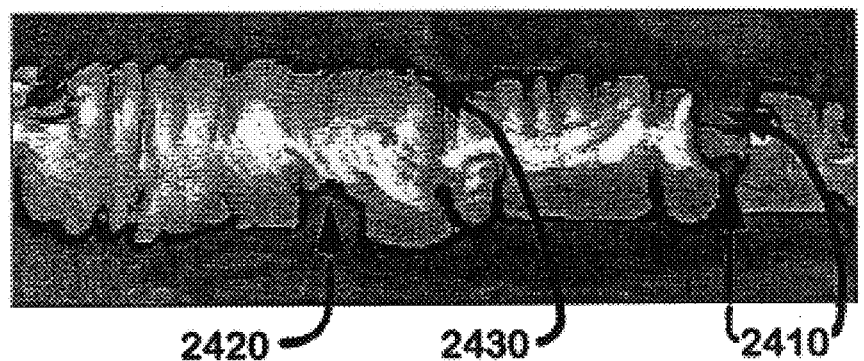
FIG. 21A demonstrates identification of three different types of lesions utilizing a soft straightened colon.
Figure 21B:
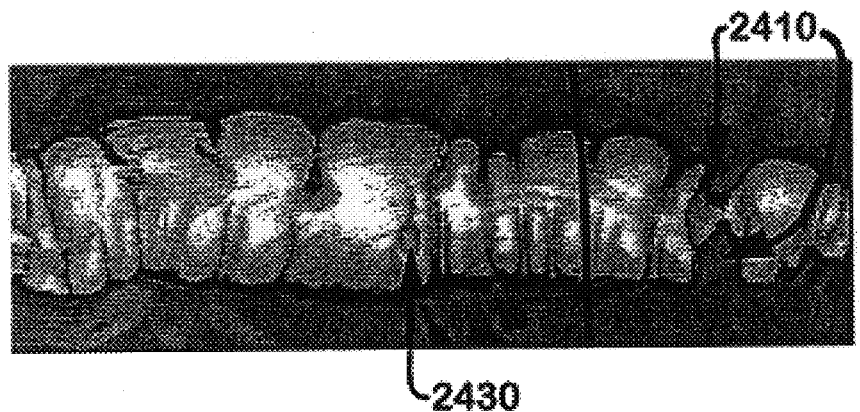
FIG. 21B shows the same as shown in FIG. 21A with the soft straightened colon being rotated 90° with respect to the central path of the colon.

Finally, FIG. 21 illustrates a colon straightened according to the present invention. FIG. 21 displays of two halves of a colon segment that was straightened with the electrical field based method from a patient CT image volume. These volume-renderings show accurate detection of three different types of lesions: circumferential cancer 2410, a large lesion of 2 cm in diameter 2420 and a small polyp 2430 of 8 mm in diameter. Segments in FIG. 21A and FIG. 21B differ by a 90° rotation with respect to the central path of the colon.

Although the present invention has been described with reference to certain preferred embodiments thereof, variations and modification of the present invention can be effected within the spirit and scope of the following claims.

What is claimed is:

1. A system for unraveling a tubular/curvilinear biological structure comprising:
   (a) a means for generating image volume data of the tubular/curvilinear biological structure; and
   (b) a processing means for performing the steps of:
      (i) determining the set of points representing the central path of the generated image volume data;
      (ii) constructing a curved cross section from each of the central path points;
      (iii) mapping the curved cross sections onto rectangular or polar coordinates;
      (iv) stacking the mapped cross sections; and
      (v) outputting the unraveled tubular/curvilinear biological structure.

2. The system of claim 1, wherein the curved cross sections are constructed by performing the substeps of:
   (1) selecting a previously unselected point on the central path;
   (2) creating a curved cross section associated with the selected point by performing the sub-substeps of:
      a) constructing a data grid through the selected point;
      b) simulating an electrical field by assigning a positive charge to a subset of the set of central path points;
      c) generating electrical force lines associated with the selected point; and
      d) mapping the data from the generated electrical force lines onto the data grid; and
   (3) repeating steps (1)–(2) until all points of interest in the set of central path points have been selected.

3. The system of claim 2, wherein the subset of points assigned a positive charge is a proper subset of the set of central path points.

4. The system of claim 2, wherein the sub-substep generating electrical force lines comprises the sub-sub-substeps of:
   i) generating representative electrical force lines associated with the selected point;
   ii) computing the functional fitting coefficients of the representative electrical force lines; and
   iii) interpolating for coefficients of additional force lines.

5. A system for unraveling a tubular/curvilinear biological structure comprising:
   (a) an output device for outputting the unraveled tubular/curvilinear biological structure;
   (b) a scanner for generating image volume data of the tubular/curvilinear biological structure; and
   (c) a processor for performing the steps of:
      (i) determining the set of points representing the central path of the generated image volume data;
      (ii) selecting a previously unselected point on the central path;
      (iii) creating a curved cross section associated with the selected point by performing the substeps of:
         (1) constructing a data grid for the selected point;
         (2) simulating an electrical field by assigning a positive charge to a subset of the set of central path points;
         (3) generating electrical force lines associated with the selected point; and
         (4) mapping the data from the generated electrical force lines onto the data grid; and
      (iv) repeating steps (ii)–(iii) until all points in the set of central path points have been selected;
      (v) stacking the mapped cross sections; and
      (vi) outputting the unraveled tubular/curvilinear biological structure to the output device.

6. The system of claim 5, wherein the subset of points assigned a positive charge is a proper subset of the set of central path points.

7. The system of claim 5, wherein the substep generating electrical force lines comprises the sub-substeps of:
   a) generating representative electrical force lines associated with the selected point;
   b) computing the functional fitting coefficients of the representative electrical force lines; and
   c) interpolating for coefficients of additional force lines.

8. A computer-readable, digital storage device storing executable instructions which cause a processor to unravel a tubular/curvilinear biological structure by:
   (a) receiving image volume data associated with the tubular/curvilinear biological structure;
   (b) determining the set of points representing the central path of the received image volume data;
   (c) constructing a curved cross section from each of the central path points;
   (d) stacking the cross sections; and
   (e) outputting the unraveled tubular/curvilinear biological structure.

9. The device of claim 8, wherein the curved cross sections are constructed by performing the substeps of:
   (i) selecting a previously unselected point on the central path;
   (ii) creating a curved cross section associated with the selected point by performing the sub-substeps of:
      (1) constructing a data grid for the selected point;
      (2) simulating an electrical field by assigning a positive charge to a subset of the set of central path points;
      (3) generating electrical force lines associated with the selected point; and
      (4) mapping the data from the generated electrical force lines onto the data grid; and
   (iii) repeating steps (i)–(ii) until all points in the set of central path points have been selected.

10. The device of claim 9, wherein the subset of points assigned a positive charge is a proper subset of the set of central path points.

11. The device of claim 9, wherein the sub-substep generating electrical force lines comprises the sub-sub-substeps of:
   a) generating representative electrical force lines associated with the selected point;
   b) computing the functional fitting coefficients of the representative electrical force lines; and
   c) interpolating for coefficients of additional force lines.

12. A method for unraveling a tubular/curvilinear biological structure comprising the steps of:
   (a) receiving image volume data associated with the tubular/curvilinear biological structure;
   (b) determining the set of points representing the central path of the received image volume data;
   (c) constructing a curved cross section from each of the central path points;
   (d) stacking the cross sections; and
   (e) outputting the unraveled tubular/curvilinear biological structure.

13. The method of claim 12, wherein the curved cross sections are constructed by performing the substeps of:
   (i) selecting a previously unselected point on the central path;
   (ii) creating a curved cross section associated with the selected point by performing the sub-substeps of:
      (1) constructing a data grid for the selected point;
      (2) simulating an electrical field by assigning a positive charge to a subset of the set of central path points;
      (3) generating electrical force lines associated with the selected point; and
      (4) mapping the data from the generated electrical force lines onto the data grid; and
   (iii) repeating steps (i)–(ii) until all points in the set of central path points have been selected.

14. The method of claim 13, wherein the subset of points assigned a positive charge is a proper subset of the set of central path points.

15. The method of claim 13, wherein the sub-substep generating electrical force lines comprises the sub-sub-substeps of:
   a) generating representative electrical force lines associated with the selected point;
   b) computing the functional fitting coefficients of the representative electrical force lines; and
   c) interpolating for coefficients of additional force lines.

* * * * *